US008067236B2

(12) United States Patent
Krohn et al.

(10) Patent No.: US 8,067,236 B2
(45) Date of Patent: Nov. 29, 2011

(54) OPTIMIZED HUMAN T1R3 NUCLEIC ACID MOLECULE

(75) Inventors: Michael Krohn, Lorsch (DE); Holger Zinke, Zwingenberg (DE)

(73) Assignee: Nutrinova Nutrition Specialties & Food Ingredients GmbH, Frankfurt (DE)

( * ) Notice: Subject to any disclaimer, the term of this patent is extended or adjusted under 35 U.S.C. 154(b) by 38 days.

(21) Appl. No.: 12/616,361

(22) Filed: Nov. 11, 2009

(65) Prior Publication Data

US 2010/0120141 A1 May 13, 2010

Related U.S. Application Data

(62) Division of application No. 11/810,402, filed on Jun. 5, 2007.

(30) Foreign Application Priority Data

Jun. 7, 2006 (EP) ..................................... 06011710

(51) Int. Cl.
*C12N 1/20* (2006.01)
*C12N 7/00* (2006.01)
*C12N 5/00* (2006.01)
*C07H 21/04* (2006.01)
*C07K 14/705* (2006.01)

(52) U.S. Cl. .................. 435/325; 435/235.1; 435/252.3; 530/350; 536/23.1; 536/23.5

(58) Field of Classification Search ........................ None
See application file for complete search history.

(56) References Cited

U.S. PATENT DOCUMENTS

| | | | |
|---|---|---|---|
| 5,010,175 A | 4/1991 | Rutter et al. | |
| 5,288,514 A | 2/1994 | Ellman | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,569,588 A | 10/1996 | Ashby et al. | |
| 5,593,853 A | 1/1997 | Chen et al. | |
| 2003/0040045 A1 | 2/2003 | Zuker et al. | |
| 2004/0191862 A1 | 9/2004 | Zoller et al. | |

FOREIGN PATENT DOCUMENTS

| WO | WO 91/19735 A1 | 12/1991 |
|---|---|---|
| WO | WO 92/00091 A1 | 1/1992 |
| WO | WO 93/20242 A1 | 10/1993 |
| WO | WO 00/06952 A1 | 2/2000 |
| WO | WO 03/025137 A2 | 3/2003 |
| WO | WO 2004/069191 A2 | 8/2004 |
| WO | WO 2005/033125 A2 | 4/2005 |

OTHER PUBLICATIONS

Skolnick et al. From genes to protein structure and function: novel applications of computational approaches in the genomic era. Trends in Biotech 18(1): 34-39, 2000.*

Bork, A. Powers and pitfalls in sequence analysis: the 70% hurdle. Genome Res 10: 398-400, 2000.*

Doerks et al. Protein annotation: detective work for function prediction. Trends in Genetics 14(6): 248-250, 1998.*

Smith et al. The challenges of genome sequence annotation or "The devil is in the details", Nature Biotech 15: 1222-1223, 1997.*

Brenner, S.E. Errors in genome function. Trends in Genetics 15(4): 132-133, 1999.*

Bork et al. Go hunting in sequence databases but watch out for the traps. Trends in Genetics. 12(10): 425-427, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 491-495, 1994.*

Kaufman et al. Blood 94: 3178-3184, 1999.*

Wang et al. Rapid analysis of gene expression (RAGE) facilitates universal expression profiling. Nucleic Acids Res 27(23): 4609-4618, 1999.*

Phillips, A., The challenge of gene therapy and DNA delivery. J Pharm Pharmacology 53: 1169-1174, 2001.*

Offermanns, S. and Simon, M. (Jun. 23, 1995) $G\alpha_{15}$ and $G\alpha_{16}$ Couple a Wide Variety of Receptors to Phospholipase C. *The Journal of Biological Chemistry*, vol. 270, No. 25, 15175-15180 The American Society for Biochemistry and Molecular Biology, Inc.

Ueda, T. et al. (Aug. 13, 2003) Functional Interaction between T2R Taste Receptors and G-Protein α Subunits Expressed in Taste Receptor Cells. *The Journal of Neuroscience*, 23(19), 7376-7380 Society for Neuroscience.

Pachuk, C. et al. (2000) Chain reaction cloning: a one-step method for directional ligation of multiple DNA fragments. *Gene* 243 19-25 Elsevier Science B.V.

Stemmer, W. et al. (1995) Single-step assembly of a gene and entire plasmid from large numers of oligodeoxyribonucleotides *Gene* 164 49-53 Elsevier Science B.V.

Jackson, R.J. et al. (1990) The novel mechanism of initiation of picornavirus RNA translation. *Trends Biochem Science* 15, 477-483 Elsevier Science Publishers Ltd. (UK).

Jang, S.K. et al. (1988) A Segment of the 5' Nontranslated Region of encephalomyocarditis Virus RNA Directs Internal Entry of Ribosomes during in Vitro Translation. *Journal of Virology*, 62 2636-2643 American Society for Microbiology.

Kitagawa, M. et al. (2001) Molecular Genetic Identification of a Candidate Receptor Gene for Sweet Taste. *Biochemical and Biophysical Research Communications*, 283, 236-242 Academic Press.

Margolskee, R. F. (2002) Molecular Mechanisms of Bitter and Sweet Taste Transduction. *The Journal of Biological Chemistry*. vol. 277, No. 1, 1-4 The American Society for Biochemistry and Molecular Biology, Inc.

Sugita, M. and Shiba, Y. (2005) Genetic Tracing Shows Segregation of Taste Neuronal Circuitries for Bitter and Sweet. Science 309, 781-785.

Kaupmann, K. et al. (Dec. 17, 1998) $GABA_B$. Nature vol. 396, 683-687 Macmillan Publishers Ltd.

Meyerhof, W. et al. (2005) Human Bitter Taste Perception. *Chemical Senses*, vol. 30, suppl 1, i14-i15 Oxford University Press.

(Continued)

*Primary Examiner* — Bridget E Bunner
(74) *Attorney, Agent, or Firm* — Kristina Bieker-Brady; Clark & Elbing LLP

(57) ABSTRACT

The present invention relates to a screening system for modulators of GPCRs. Further it relates to recombinant vector systems for the heterologous expression of heterodimeric g-protein coupled receptors (GPCRs) in eukaryotic host cells. Preferably the functional expression of engineered GPCRs for the perception of sweet and L-amino acid taste or more preferably the use of these receptors for the identification of functional ligands is also encompassed.

5 Claims, 4 Drawing Sheets

OTHER PUBLICATIONS

Fux, C. et al. (2004) New-Generation Multicistronic Expression Platform: Ptrident Vectors Containing Size-Optimized IRES Elements Enable Homing endonuclease-Based Cistron Swapping into Lentiviral Expression Vectors. *Wiley InterScience* (www.interscience.wiley.com) 174-187 Wiley Periodicals, Inc.

Hellen, C. and Sarnow, P. (2001) Internal ribosome entry sites in eukaryotic mRNA molecules. *Genes & Development* 15 1593-1612 Cold Spring Harbor Laboratory Press.

Fussenegger, M. et al. (Jan. 5, 1998) pTRIDENT, a Novel Vector Family for Tricistronic Gene Expression in Mammalian Cells. *Biotechnology and Bioengineering*, vol. 57, No. 1, 1-10 John Wiley & Sons, Inc.

Hartenbach, S. and Fussenegger, M. (2005) Autoregulated, bidirectional and multicistronic gas-inducible mammalian as well as lentiviral expression vectors. *Journal of Biotechnology*, BIOTEC-3980, 1-16 Science Direct.

Kramer, B.P. et al. (Sep. 30, 2003) Artificial Regulatory Networks and Cascades for Discrete Multilevel Transgene Control in Mammalian Cells. *Biotechnology and Bioengineering*, vol. 83, No. 7, 810-820 Wiley Periodicals, Inc.

Moser, S. et al. (2000) An Update of pTRIDENT Multicistronic Expression Vectors: pTRIDENTs Containing Novel Streptogramin-Responsive Promoters. *Piotechnol. Prog.* vol. 16, No. 5, 724-735 American Chemical Society and American Institute of Chemical Engineers.

Weber, W. et al. (2005) Engineered *Streptomyces* quorum-sensing components enable inducible siRNA-mediated translation control in mammalian cells and adjustable transcription control in mice. *J Gene Medicine* 7, 518-525 John Wiley & Sons, Ltd.

Elgen, R. M. (2005) An Overview of High Throughput Screening at G Protein Coupled Receptors. *Frontiers in Drug Design & Discovery* 1, 97-111 Bentham Science Publishers.

Filmore, D. (Nov. 2004) It's a GPCR World. *Modern Drug Discovery* American Chemical Society.

Offermanns, W. et al. (2003) G-proteins as transducers in transmembrane signalling. *Progress in Biophysics & Molecular Biology*, vol. 83, 101-130 University of Heidelberg, Heidelberg, Germany.

Lindemann, B., (Jul. 1996) Taste Reception. *Physiological Reviews* vol. 76, No. 3, 719-225 Saarland University, Homburg, Germany.

Montmayeur, J. et al. (2001) A candidate taste receptor gene near a sweet taste locus. *nature neuroscience*, vol. 4, No. 5, 492-498 Nature Publishing Group, Boston, Massachusetts.

Sainz, E. et al. (2001) Identification of a novel member of the T1R family of putative taste receptors. *Journal of Neurochemistry* 77; 896-903 International Society for Neurochemistry, Rockville, USA.

Pin, J. et al. (2003) Evolution, structure, and activation mechanism of family 3/C G-protein-coupled receptors. *Pharmacology & Therapeutics* 98 325-354 Science Direct, France.

Bai, M. et al. (Sep. 4, 1998) Dimerization of the Extracellular Calcium-sensing Receptor (CaR) on the Cell Surface of CaR-transfected HEK293 Cells. *The Journal of Biological Chemistry* vol. 273, No. 36, 23605-23610 The American Society for Biochemistry and Molecular Biology, Inc., USA.

Kunishima, N. et al. (Oct. 26, 2000) Structural basis of glutamate recognition by a dimeric metabotropic glutamate receptor. *Nature* vol. 407, 971-977 Macmillan Magazines Ltd.

White, J. H. et al. (Dec. 17, 1998) Heterodimerization is required for the formation of a functional $GABA_B$ receptor. *Nature* vol. 396, 679-682 Macmillan Publishers Ltd.

Li, X. et al. (Apr. 2, 2002) Human receptors for sweet and umami taste. *PNAS* vol. 99, No. 7, 4692-4696 Senomyx, Inc. La Jolla, CA and Aurora Biosciences Corp., San Diego, CA.

Nelson, G. et al. (Mar. 14, 2002) An amino-acid taste receptor. *Nature* vol. 416, 199-202 Macmillan Magazines Ltd.

Nelson, G. e al. (Aug. 10, 2001) Mammalian Sweet Taste Receptors. *Cell* vol. 106, 381-390 Cell Press.

Zhao, F. et al. (2002) Dual actions of caffeine on voltage-dependent currents and intracellular calcium in taste receptor cells. *Am J Physiol Regulatory Integrative Comp Physiol* 283, R115-R129 The American Physiological Society.

Hood, M.A. et al. (Feb. 19, 1999) Putative mammalian Taste Receptors: A Class of Taste-Specific GPCRs with Distinct Topographic Selectivity. *Cell*, vol. 96; 541-551 University of California, La Jolla, California.

Hood, M.A. and Ryba, N.J.P. (Apr. 1997) Analysis and Comparison of Partial Sequences of Clones from a Taste-bud-enriched cDNA Library. *J. DentRes*, 76(4) 831-838 National Institute of Dental Research, Bethesda, Maryland.

Kitagawa, M. et al. (2001) Molecular Genetic Identification of a Candidate Receptor Gene for Sweet Taste. *Biochemical and Biophysical Research Communications* 283; 236-242 Academic Press, Japan.

Li, X. et al. (2001) High-resolution genetic mapping of the saccharin preference locus (*Sac*) and the putative sweet taste receptor (T1R1) gene (*Gpr70*) to mouse distal Chromosome 4. *Mammalian Genome* 12 13-16.

Firestein, S., (Sep. 13, 2001) How the olfactory system makes sense of scents. *Nature* vol. 413, 211-218 Columbia University, New York, NY.

Lindemann, B., (1996) Tasting the sweet and the bitter. *Current Biology* vol. 6, No. 10, 1234-1237 Saarland University, Homburg, Germany.

Lindemann, B., (Sep. 13, 2001) Receptors and transduction in taste. *Nature* vol. 413, 219-225, Saarland University, Homburg, Germany.

Kinnamon, S. and Margolskee, R. (1996). Mechanisms of taste transduction. *Current Opinion in Neurobiology*. 6, 506-513 Colorado State University, Ft. Collins, Colorado; University of Colorado, Denver, Colorado; The Mount Sinai School of Medicine, New York, NY.

Bachmanov, A. A., et al. (2001) Sweetener Preference of C57BL/6ByJ and 129P3/J Mice. *Chemical Senses* 26, 905-913 Monell Chemical Senses Center, Philadelphia, PA.

Max, M. et al. (2001) Tas1r3, encoding a new candidate taste receptor, is allelic to the sweet responsiveness locus Sac. *nature genetics* 28, 58-63 Nature Publishing Group, USA.

Brockaert, J & Pin; J. P. (1999) Molecular tinkering of G protein-coupled receptors: an evolutionary success. *The EMBO Journal*, vol. 18 No. 7; 1723-1729 France.

Pierce, K.L. et al. (Sep. 2002) Seven-transmembrane Receptors. *Nature Reviews*/Molecular Cell Biology, vol. 3; 639-650 Duke University, Durham, North Carolina.

George, S.R. et al. (Oct. 2002) G-Protein-Coupled Receptor Oligomerization and its Potential for Drug Discovery. *Nature Reviews/Drug Discovery* vol. 1; 808-820 University of Toronto, Ontario, Canada.

Milligan, G. et al. (2003) GPCR dimerisation. *Life Sciences* 74 181-188 University of Glasgow, Scotland.

Salahpour, A., et al. (2000) Functional Significance of Oligomerization of G-protein-coupled Receptors. *TEM* vol. 11, No. 5 163-168 University of Montreal, Quebec, Canada.

Maeda, T., et al. (2003) Rhodopsin phosphorylation: 30 years later. *Progress in Retinal and Eye Research* 22, 417-434 University of Washington, Seattle, WA.

Buck, L. and Axel, R., (Apr. 5, 1991) A Novel Multigene Family May Encode Odorant Receptors: A Molecular Basis for Odor Recognition. *Cell* vol. 65, 175-187 Columbia University, New York, NY.

Kinnamon, S. and Cummings, T. (1992) Chemosensory Transduction Mechanisms in Taste. *Annual Review Physiol*. 54, 715-731 Colorado State University, Ft. Collins, Colorado and University of Colorado, Denver, Colorado.

McLaughlin, S. et al. (Jun. 18, 1992). Gustducin is a taste-cell-specific G protein closely related to the transducins. *Nature* vol. 357, 563-569 Roche Institute of Molecular Biology, Nutley, New Jersey.

Wong, G.T., et al. (Jun. 27, 1996) Transduction of bitter and sweet taste by gustducin. *Nature* vol. 381, 796-800 The Mount Sinai School of Medicine, New York, NY.

Lush, I.E., et al. (1989) The genetics of tasting in mice VI. Saccharin, acesulfame, dulcin and sucrose. *Genetical Research*, 53, 95-99 University College London, London, England.

Lush, I.E., et al. (1995) The genetics of tasting in mice VII. Glycine revisited, and the chromosomal location of *Sac* and *Soa*. *Genetical Research*, 66, 167-174 University College London, London, England and National Institute for Medical Research, London, England.

U.S. Appl. No. 11/810,402, filed Jun. 5, 2007, Krohn et al.
U.S. Appl. No. 12/616,340, filed Nov. 11, 2009, Krohn et al.

\* cited by examiner

| 1 | 2 | 3 | 4 | 5 | 6 | 7 | Distance Matrix | |
|---|---|---|---|---|---|---|---|---|
| 0.00 | 11.85 | 14.64 | 44.88 | 48.59 | 51.61 | 49.96 | 1 | opt_hT1R2 |
| | 0.00 | 24.48 | 46.94 | 52.21 | 52.54 | 52.90 | 2 | sh_T1R2 |
| | | 0.00 | 44.61 | 51.67 | 54.01 | 51.59 | 3 | wt_hT1R2 |
| | | | 0.00 | 52.04 | 54.57 | 51.91 | 4 | wt_hT1R1 |
| | | | | 0.00 | 14.05 | 14.19 | 5 | opt_hT1R3 |
| | | | | | 0.00 | 23.56 | 6 | sh_T1R3 |
| | | | | | | 0.00 | 7 | wt_hT1R3 |

SEQUENCE LISTING

<160> NUMBER OF SEQ ID NOS: 4

<210> SEQ ID NO 1
<211> LENGTH: 839
<212> TYPE: PRT
<213> ORGANISM: Homo sapiens

<400> SEQUENCE: 1

```
Met Gly Pro Arg Ala Lys Thr Ile Cys Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
        355                 360                 365
```

```
Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
    610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
        675                 680                 685

Lys Met Val Ile Val Ile Gly Met Leu Ala Thr Gly Leu Ser Pro
    690                 695                 700

Thr Thr Arg Thr Asp Pro Asp Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
    770                 775                 780

Gly Val Leu Val Thr Ile Val Asp Leu Leu Val Thr Val Leu Asn Leu
```

-continued

```
                785                 790                 795                 800
Leu Ala Ile Ser Leu Gly Tyr Phe Gly Pro Lys Cys Tyr Met Ile Leu
                    805                 810                 815

Phe Tyr Pro Glu Arg Asn Thr Pro Ala Tyr Phe Asn Ser Met Ile Gln
                    820                 825                 830

Gly Tyr Thr Met Arg Arg Asp
                    835

<210> SEQ ID NO 2
<211> LENGTH: 852
<212> TYPE: PRT
<213> ORGANISM: Homo sapiens

<400> SEQUENCE: 2

Met Leu Gly Pro Ala Val Leu Gly Leu Ser Leu Trp Ala Leu Leu His
  1               5                  10                  15

Pro Gly Thr Gly Ala Pro Leu Cys Leu Ser Gln Gln Leu Arg Met Lys
                 20                  25                  30

Gly Asp Tyr Val Leu Gly Gly Leu Phe Pro Leu Gly Glu Ala Glu Glu
             35                  40                  45

Ala Gly Leu Arg Ser Arg Thr Arg Pro Ser Ser Pro Val Cys Thr Arg
         50                  55                  60

Phe Ser Ser Asn Gly Leu Leu Trp Ala Leu Ala Met Lys Met Ala Val
 65                  70                  75                  80

Glu Glu Ile Asn Asn Lys Ser Asp Leu Leu Pro Gly Leu Arg Leu Gly
                 85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
```

```
                    325                 330                 335
Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
            355                 360                 365

Arg Cys Pro Gln Cys Asp Cys Ile Thr Leu Gln Asn Val Ser Ala Gly
            370                 375                 380

Leu Asn His His Gln Thr Phe Ser Val Tyr Ala Val Tyr Ser Val
385                 390                 395                 400

Ala Gln Ala Leu His Asn Thr Leu Gln Cys Asn Ala Ser Gly Cys Pro
            405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
            435                 440                 445

Asn Val Asp Met Glu Tyr Asp Leu Lys Leu Trp Val Trp Gln Gly Ser
            450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
            485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
            515                 520                 525

Tyr Arg Gln Asn Pro Asp Asp Ile Ala Cys Thr Phe Cys Gly Gln Asp
            530                 535                 540

Glu Trp Ser Pro Glu Arg Ser Thr Arg Cys Phe Arg Arg Ser Arg
545                 550                 555                 560

Phe Leu Ala Trp Gly Glu Pro Ala Val Leu Leu Leu Leu Leu Leu Leu
            565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
            595                 600                 605

Phe Gly Leu Val Cys Leu Gly Leu Val Cys Leu Ser Val Leu Leu Phe
            610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
            645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
            675                 680                 685

Met Leu Val Glu Val Ala Leu Cys Thr Trp Tyr Leu Val Ala Phe Pro
            690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
            725                 730                 735

Asn Ala Thr Leu Ala Phe Leu Cys Phe Leu Gly Thr Phe Leu Val Arg
            740                 745                 750
```

```
Ser Gln Pro Gly Arg Tyr Asn Arg Ala Arg Gly Leu Thr Phe Ala Met
        755                 760                 765
Leu Ala Tyr Phe Ile Thr Trp Val Ser Phe Val Pro Leu Leu Ala Asn
770                 775                 780
Val Gln Val Val Leu Arg Pro Ala Val Gln Met Gly Ala Leu Leu Leu
785                 790                 795                 800
Cys Val Leu Gly Ile Leu Ala Ala Phe His Leu Pro Arg Cys Tyr Leu
                805                 810                 815
Leu Met Arg Gln Pro Gly Leu Asn Thr Pro Glu Phe Phe Leu Gly Gly
            820                 825                 830
Gly Pro Gly Asp Ala Gln Gly Gln Asn Asp Gly Asn Thr Gly Asn Gln
        835                 840                 845
Gly Lys His Glu
    850

<210> SEQ ID NO 3
<211> LENGTH: 2523
<212> TYPE: DNA
<213> ORGANISM: Artificial Sequence
<220> FEATURE:
<223> OTHER INFORMATION: Multiparameter optimized nucleic acid molecule

<400> SEQUENCE: 3
atgggcccta gagccaagac aatctgcagc ctgttttttcc tgctgtgggt gctggccgag      60
cccgccgaga atagcgactt ttacctgccc ggcgactatc tgctgggcgg cctgttcagc     120
ctgcacgcca atatgaaggg gatcgtgcac ctgaattttc tgcaagtccc aatgtgtaaa     180
gaatacgaag tgaaagtgat cggctacaat ctgatgcagg ctatgagatt tgccgtggag     240
gaaatcaata cgactcctc cctgctgccc ggcgtgctcc tcggctacga gattgtggac     300
gtctgttaca tcagcaacaa cgtgcagccc gtgctgtatt ttctggccca cgaggataat     360
ctgctgccta tccaggagga ttactccaac tacatcagcc gcgtggtggc cgtgatcggc     420
cccgacaaca gcgagagcgt gatgaccgtg gccaattttc tgagcctgtt cctgctgccc     480
cagatcacat actccgccat ctccgacgag ctgagggaca agtgagatt ccccgccctg     540 ctgagaacca ccccttctgc cgatcaccat gtggaagcta tggtccagct catgctccat     600
ttccgctgga attggattat cgtcctggtg tcctccgata cctacggcag agataacgga     660
cagctgctgg gagagcgcgt ggccagacgg gatatctgta ttgcctttca ggaaaccctg     720
cctaccctgc agcctaatca gaatatgacc agcgaggagc ggcagagact cgtgacaatc     780
gtggataaac tccagcagtc caccgccaga gtggtggtgg tgttcagccc cgatctgaca     840
ctgtatcatt ttttttaacga agtgctgagg caaaatttca ccggggctgt gtggattgcc     900
agcgaaagct gggccattga tcccgtgctg cacaatctga ccgaactggg gcacctgggc     960
acatttctcg ggatcacaat ccagtccgtg cctatccctg cttttccga gttcagggag    1020 tggggacctc aggccggacc cccccactg agcagaacct cccagtccta cacctgtaat    1080
caggagtgtg ataattgtct gaatgccacc ctgagcttca ataccatcct gcggctgagc    1140
ggcgagagag tggtgtactc cgtgtacagc gccgtgtacg ccgtgcccca cgctctgcac    1200
tccctgctgg gctgcgataa gtccacctgc acaaagcgcg tggtgtatcc ttggcagctc    1260
ctggaggaaa tttggaaagt gaacttcacc ctgctggatc atcagatctt ctttgacccc    1320
cagggcgatg tggcactgca cctggaaatc gtgcaatggc agtgggacag atcccagaac    1380 cccttttcagt ccgtggccag ctactatcct ctccagaggg agctcaagaa tatccaggat    1440
atcagctggc acacagtgaa taataccatc cccatgagca tgtgcagcaa gagatgccag    1500
```

```
agcggccaga agaagaaacc cgtggggatt cacgtgtgct gttttgagtg tattgattgc      1560
ctgcctggga ccttcctgaa tcacaccgag gacgagtacg agtgtcaggc ctgtcccaac      1620
aatgagtgga gctaccagtc cgagaccagc tgctttaagc gccagctcgt gtttctggag      1680
tggcacgagg cccctacaat gccgtggca ctgctggctg ctttgggctt tctgtccaca       1740
ctggctattc tggtgatctt ttggagacac tttcagaccc ccatcgtgag aagcgccgga      1800
ggccctatgt gttttctcat gctcaccctg ctgctcgtcg cctatatggt ggtgcccgtg      1860
tatgttggcc ctcccaaagt gagcacctgc ctgtgtagac aggccctgtt ccccctgtgt      1920
ttcaccatct gcatcagctg catcgccgtg aggagctttc agatcgtgtg tgcttttaag      1980
atggcctccc ggttccccag agcctactcc tactgggtga gataccaggg cccttacgtg      2040
agcatggcct tcatcaccgt gctgaagatg gtgatcgtgg tcatcgggat gctggctacc      2100
ggcctgagcc ctaccaccag aaccgacccc gacgatccta agattaccat cgtgagctgc      2160
aaccccaatt acaggaactc cctgctgttt aatacctctc tggatctgct gctgagcgtg      2220
gtgggcttct ctttcgccta tgggggaag gaactgccta ccaattacaa tgaagctaag      2280
tttatcaccc tgtccatgac cttttacttc acaagcagcg tgagcctgtg caccttatg      2340 agcgcctact ccggcgtgct ggtgacaatc gtcgatctgc tggtgaccgt gctgaatctg      2400
ctggccatct ctctgggcta ttttgggcct aagtgttaca tgattctgtt ttaccccgag      2460
aggaacaccc ctgcctactt taattccatg attcagggct acacaatgcg gcgcgactga      2520
taa                                                                    2523

<210> SEQ ID NO 4
<211> LENGTH: 2582
<212> TYPE: DNA
<213> ORGANISM: Artificial Sequence
<220> FEATURE:
<223> OTHER INFORMATION: Multiparameter optimized nucleic acid molecule

<400> SEQUENCE: 4
atgctgggac cgccgtgct gggcctgtcc ctgtgggcac tgctgcaccc cggcacaggc         60
gcccctctgt gcctgagcca gcagctgaga atgaagggcg attatgtgct cggcggcctg       120
tttcctctgg gcgaagccga agaagccggc ctgaggagca gaaccagacc tagctccccc       180
gtgtgcacaa gattcagcag caacgggctg ctgtgggccc tcgctatgaa gatggccgtc       240
gaggaaatca ataataagag cgacctgctg cctggcctga gactgggcta tgacctgttc       300
gacacctgca gcgaacccgt ggtggctatg aaaccctccc tgatgttcct ggccaaagcc       360
ggcagcagag atattgccgc ctattgtaat tacacccagt atcagcctag agtgctggcc       420
gtgatcggcc ctcacagcag cgagctggcc atggtgacag ggaagttttt cagcttttt       480 ctgatgcccc aagtgagcta tggcgcctcc atgaactgc tgtccgccag agagacattc       540
cccagcttct tcaggacagt gccctccgat agagttcagc tgaccgccgc tgccgaactg       600
ctgcaggaat ttggatggaa ttgggtcgca gctctgggct ccgatgatga gtacggcaga       660
caggggctga gcattttcag cgccctggct gccgccagag catctgtat tgcccatgag       720 ggactggtgc cctgcctag agccgatgat agccggctgg gcaaagtcca ggatgtgctg       780
caccaagtga atcagtcctc cgtgcaagtg gtcctgctct ttgccagcgt gcatgccgcc       840 catgcccctgt tcaattactc catcagcagc cgcctgagcc ctaaagtgtg ggttgcctcc       900
gaggcttggc tgacaagcga tctggtgatg ggcctgcctg gatggctca aatgggcacc       960 gtgctgggct ttctgcagag aggcgctcag ctccacgaat tcctcagta tgtgaaaacc      1020
```

```
catctggccc tcgccacaga tcctgccttc tgcagcgccc tgggagaaag agaacagggc    1080
ctggaggaag atgtggtcgg acagagatgc cctcagtgcg attgtattac cctgcagaac    1140
gtgtctgccg gcctgaatca ccatcagacc ttcagcgtgt acgccgccgt gtactccgtg    1200
gctcaggctc tgcacaatac cctgcagtgt aacgccagcg gctgccctgc ccaggatcct    1260
gtgaaccttt ggcagctgct cgagaatatg tataatctga catttcacgt gggaggcctg    1320
cccctgagat tcgatagctc cggcaatgtg gatatggaat atgatctgaa actgtgggtc    1380
tggcaaggca gcgtgcctag actgcacgat gtgggccgct ttaacggctc tctgcggacc    1440
gagaggctga agattagatg gcacaccagc gacaatcaga agcctgtgag ccggtgcagc    1500
agacagtgtc aggagggaca agtgcggaga gtgaagggct tccacagctg ctgttacgac    1560
tgcgtggatt gtgaggccgg ctcctacaga cagaaccccg atgatatcgc ctgtaccttc    1620
tgcggacagg acgagtggag ccctgagaga agcaccagat gcttccggcg gaggagcaga    1680
tttctggcct ggggagaacc cgctgtgctg cttctgctgt tgctgctctc tctggccctg    1740
ggactggtgc tggccgcact gggcctgttt gtgcaccaca gagacagccc cctggtgcag    1800
gccagcggcg gacctctggc ctgtttcggg ctcgtgtgtc tgggccttgt gtgtctgagc    1860
gtgctgctct ttccaggcca gccttcccca gctagatgtc tggctcagca acccctgagc    1920
cacctgcccc tgaccggctg tctgagcacc ctgtttctcc aggccgctga gatctttgtg    1980
gagagcgagc tgccgctgtc ttgggccgac agactgagcg gctgtctgag aggcccctgg    2040
gcttggctgg ttgtcctcct ggctatgctg gttgaagtgg ccctgtgtac ctggtatctg    2100
gtcgcctttc cacccgaagt ggtgaccgat tggcatatgt tgcctaccga ggccctggtg    2160
cactgtagaa ccaggagctg ggtgagcttt ggactggccc acgccacaaa cgccacccctg    2220 gccttcctgt gtttcctggg gacctttctg gtgagaagcc agcccggcag atacaataga    2280
gccaggggcc tgacattcgc catgctcgct tactttatta catgggtgag cttcgtgcct    2340
ctgctggcca acgtgcaagt tgtgctgcgc cctgccgtgc aaatgggagc actgctgctg    2400
tgcgtgctgg gcattctggc cgcttttcat ctgccccgct gctatctgct gatgagacag    2460
cccggcctga ataccccctga gtttttttctg ggcggaggcc ctggcgacgc ccagggacag    2520
aacgacggca acaccggcaa ccagggcaag cacgagtgat aagagaccgc ggccgctgat    2580
ca                                                                  2582
```

OPTIMIZED HUMAN T1R3 NUCLEIC ACID MOLECULE

CROSS-REFERENCE TO RELATED APPLICATIONS

This application is a divisional of co-pending U.S. application Ser. No. 11/810,402, filed Jun. 5, 2007. Co-pending U.S. application Ser. No. 11/810,402 is hereby incorporated by reference herein in its entirety. This application further claims priority to its parent application, European Patent Application No. 06011710.8 filed Jun. 7, 2006 which is also hereby incorporated by reference herein in its entirety.

FIELD OF THE INVENTION

The present invention relates to a screening method for the identification of modulators (agonists as well as antagonists) of selected GPCRs and the thus identified modulators. In a preferred embodiment of the present invention these modulators may be taste modulators. The present invention relates further to recombinant vector systems for the stable, heterologous expression of selected heterodimeric g-protein coupled receptors (GPCRs) in eucaryotic host cells. The functional expression of engineered GPCRs for the perception of sweet and L-amino acid taste and the use of said receptors for the identification of functional ligands is disclosed.

BACKGROUND OF THE INVENTION

In this specification, a number of documents are cited. The disclosure of these documents, including manufacturer's manuals and patent applications or patents, is herewith incorporated by reference in its entirety.

GPCRs represent the largest family of cell surface receptors with an estimated number of up to 1000 genes within the human genome characterized by a seven-transmembrane configuration as their main feature. (Bockaert and Pin, 1999; Pierce et al., 2002). GPCRs are activated by a multitude of different ligands, including peptides, proteins, lipids, small molecules, ions or even photons. Activated GPCRs alter their conformation allowing it to catalyze the exchange of guanosine diphosphate (GDP) for guanosine triphosphate (GTP) on the α-subunit of a heterotrimeric g-protein coupled to the GPCR. Heterotrimeric G-proteins composed of one out of 18 different α-subunits, one out of 5 different β-subunits and one out of 11 different γ-subunits are usually classified by the nature of their α-subunit and generally grouped into four main classes: $G_s$, which activates adenylyl cyclase; $G_i$, which inhibits adenylyl cyclase; $G_q$, which activates phospholipase C; and $G_{12/13}$ with heterologous functions. In addition to the α-subunit dependent signaling the β/γ-subunits can function as signaling molecules on their own. GPCR dependent signaling becomes even more complex if it is considered that these receptors can exist as homo-oligomeric or hetero-oligomeric complexes. (George et al., 2002; Milligan et al., 2003; Salahpour et al., 2000). Hence, it is not surprising that GPCRs are responsible for the regulation of a wide variety of different physiological processes.

Recently the role of GPCRs in human senses like vision, olfaction and taste has been subject of intensified investigations. While the participation of the GPCR rhodopsin in visual sensing is one of the most comprehensively examined g-protein coupled receptor signaling examples of the last 30 years (Maeda et al., 2003), the role of GPCRs in olfaction and bitter taste as well as sweet taste was discovered in the 1990ies. (Buck and Axel, 1991; Firestein, 2001; Lindemann, 1996b; Lindemann, 2001).

The discovery of GPCR signaling in taste perception is closely connected to the discovery of tastant specific signaling in vertebrate taste cells. In electrophysical and biochemical studies it was apparent that tastant derived signaling resulted in typical GPCR dependent second messenger induction, e.g. cyclic nucleosides (cAMP, cGMP), inositol triphosphate (IP3) or calcium. (Kinnamon und Cummings, 1992; Kinnamon und Margolskee, 1996; Lindemann, 1996a). The participation of GPCRs in taste perception was further approved by the finding of the g-protein gustducin specifically expressed in vertebrate taste cells. (McLaughlin et al., 1992; Wong et al., 1996). On the other hand it was known from genetic mouse studies that the ability to sense sweet taste of e.g. saccharin was linked to the so called sac locus on mouse chromosome 4. (Bachmanov et al., 2001; Lush, 1989; Lush et al., 1995). Based on these data it was obvious to search for GPCR sequence tags in taste cell derived subtracted cDNA libraries or by performing genomic sequence scanning to further narrow down the mouse sac locus for the identification of GPCR analogs as putative taste receptors. These two approaches led to the rat, mouse and human receptor DNA sequences for the taste GPCRs T1R1 and T1R2 (Hoon et al., 1999; Hoon and Ryba, 1997) as well as T1R3. (Kitagawa et al., 2001; Li et al., 2001; Max et al., 2001; Montmayeur et al., 2001; Sainz et al., 2001). Homology alignments revealed that these taste receptors like the homodimeric metabotrophic glutamate receptor (mGluR), the heterodimeric γ-aminobutyric acid type B receptor ($GABA_BR$) and homodimeric extracellular calcium receptors are members of the small family of class C GPCRs. As a common characteristic most of the class C receptors exhibit a large extracellular amino terminal domain composed of a so called venus flytrap module (VFTM) and a cysteine rich domain (CRD) that connects the VFTM to the heptahelical domain. (Pin et al., 2003). Besides that homo- as well as hetero-oligomerisation was described for several of these class C receptors. (Bai et al., 1998; Kaupmann et al., 1998; Kunishima et al., 2000; White et al., 1998). Consequently, the characteristic feature of GPCR oligomerisation of class C receptors was tested for the putative sweet taste receptors T1R1, T1R2 and T1R3.

By recombinant heterologous expression in eucaryotic cell systems a functional expression and tastant specific activation of an artificially linked G-Protein dependent signaling cascade was demonstrated by calcium imaging. T1R receptors assemble to build up functional taste receptors. As a result of several investigations it was shown that the heterodimeric T1R1/T1R3 functions as a glutamate (umami) and L-amino acid receptor whereas the heterodimeric T1R2/T1R3 functions as a high affinity sugar and artificial sweetener receptor. Particularly, heterodimeric co-expression of T1R1 and T1R3 results in taste receptors that respond to umami taste and monosodium glutamate stimuli whereas heterodimeric co-expression of T1R2 and T1R3 results in taste receptors that respond to sweet stimuli like diverse sugars (e.g. glucose and sucrose), artificial sweetener (e.g. acesulfam K, cyclamat, saccharin) and sweet proteins like monellin, thaumatin, brazzein (Li et al., 2002; Nelson et al., 2002; Nelson et al., 2001; Zhao et al., 2002). A similar chronicle could be generated for the identification of GPCRs for the perception of bitter taste with the exception that so far no homo- or oligo-merisation has been reported for these so called T2R-GPCRs. (Meyerhof et al., 2005).

The above discussed identification of genes coding for receptors responsible e.g. for taste perception, together with cloning said genes into appropriate vectors for the expression of said proteins in eukaryotic cells and the transformation of said cells with said vectors raised the expectation that screening systems and/or screening methods for GPCR modulators, i.e. agonists and antagonists of the above detailed receptors should be easy to be developed within a reasonable time.

This is reflected by a huge and still growing number of patent applications in this field.

The cloning of T1R1 is disclosed in different patent applications, e.g. in WO 03/025137; in WO 00/06952 (wherein it is designated GPCR-B3) US020040191862A1 and WO2005/033125.

The cloning of T1R2 is disclosed in patent applications WO 03/025137, US020040191862A1 and US020030040045A1

The cloning of T1R3 is disclosed in patent applications WO 03/025137, WO 03/025137, US020040191862A1 and US020030040045A1

A system for the expression of said proteins in eukaryotic cells is disclosed in patent applications WO 03/025137, WO 00/06952, US20040191862A1, WO2004069191 and US20030040045A1.

A screening system for putative taste modulators is disclosed in patent applications WO 00/06952, WO2004069191 and US20030040045A1.

Yet, nothing is to be told about the successful identification of new modulators, e.g. new artificial taste modulators such as new sweeteners utilizing such screening methods/systems.

The ongoing debate on obesity in developed countries and the growing health consciousness of consumers lead to an increasing demand of food and beverages with significant calorie reduction compared to products fully sweetened with carbohydrates such as sucrose, glucose, fructose or syrups such as HFCS 55 or 42. As the consumer usually is not willing to compromise on taste products should have similar sweetness intensity and taste quality as products regularly sweetened with these carbohydrates.

High intensity sweeteners are substances, which have no or virtually no calories and a sweetness potency several times higher than sugar. High intensity sweeteners or blends of high intensity sweeteners are used in food and beverages to achieve a sweet taste without adding calories to the products.

Most commonly used high intensity sweeteners are not from natural origin; They were discovered accidentally and are chemically synthesized. Most of them have a widespread approval in a large number of countries. Examples are substances such as acesulfame K, alitame, aspartame, cyclamate, neohesperidine dihydrochalcone, neotame, saccharin, and sucralose.

However, no high-intensity sweetener matches the taste profile of sugar completely. They differ in characteristics such as sweetness profile, side taste and off-taste characteristics. Proper blending of different high intensity sweeteners is known to overcome part of the taste limitations of single high-intensity sweeteners. But even if a more sugar-like sweetness profile is achieved in products with high-intensity sweeteners only, they still can be distinguished sensorically from their counterparts with just sugar or other carbohydrates by lack of mouthfeel and reduced flavour characteristics. Therefore a need exists for new high-intensity sweeteners which offer either alone or in blends with existing sweeteners sweetness profiles and flavour characteristics much closer to sugar than the existing products can offer.

Besides calorie reduction many of today's consumers are seeking for food and beverage products either without artificial additives or even being fully organic. Theoretically natural high-intensity sweeteners could fulfil this demand. A number of natural high-intensity sweeteners were discovered throughout past years such as stevioside, rebaudioside, brazzein, thaumatin, mogroside, glycyrrhizin, monatin, abrusoside, monellin, phyllodulcin and others. These are substances which naturally occur in different plants and can be obtained by selective extraction measures. Besides very limited approvals and in some cases difficulties to extract products on an industrial scale none of these products can claim to offer a sugar-like taste. In fact, all of these substances show a sweetness with a far slower onset than sucrose and a very lingering sweetness. Most of these products have strong sidetaste and aftertaste characteristics such as bitter, mentholic or liquorice notes or show even strong cooling or numbing sensations. Therefore some of these products, e.g. thaumatin, can be rather regarded as being flavour enhancer than sweetener. Blending of two or more of these substances can not overcome these taste limitations. Therefore in the area of natural sweetener the need for new high-intensity sweeteners with a taste profile closer to sugar is even stronger than in the case of artificial sweeteners (O'Brien Nabors, 2001; Leatherhead Food R A, 2000; Grenby, 1996; von Rymon Lipinski und Schiweck, 1991).

Therefore, there still exists a need in the art to identify and isolate new substances which may be used as modulators of taste perception, e.g. as sweeteners.

Notwithstanding the above, because of the high importance of these GPCRs in vivo, and the many different functions associated with said receptors, it has to be assumed that many of the modulators of GPCRs that might be identified by the method of the present invention may be of practical value.

Therefore, the availability of a simple and reliable screening system for modulators of said receptors would be of big importance.

In multicistronic expression vectors the coding sequences of different proteins are under the control of only one promoter and the different cistrons are connected via virus derived internal ribosomal entry sites (IRES) or cap independent translation enhancer (CITE). IRES or CITE elements confer a translation initiation independent from the otherwise necessary 5'-end of a messenger RNA, which is recognized by the eucaryotic ribosomes to start their scanning process for the first accessible translational start codon. (Fux et al., 2004; Hellen and Sarnow, 2001). So far multicistronic expression vectors have been described basically as dicistronic expression units for the coupled expression of a gene of interest linked via an cap-independent translation initiation site to a resistance marker (conferring resistance to e.g. hygromycin, zeocin, neomycin) enabling selection of stable cell lines for heterologous mammalian expression studies. For this approach IRES or CITE dependent expression vectors are commercially available.

Reports on genuine multicistronic expression studies in mammalian systems with descriptions of tri-cistronic or even quadro-cistronic heterologous expression studies are rare and for the most part intended to improve inducible protein expression e.g. for gene therapy applications. However in this pioneering work multicistronic expressions have been mostly performed with small and soluble proteins like reporter genes (green fluorescent protein, yellow fluorescent protein, red fluorescent proteins, secreted alkaline phosphatase, secreted amylase) or engineered transactivators e.g. for macrolide- or streptogramin dependent expression or selection markers. Although these studies are aimed at potential therapeutic protein expression in gene therapy applications, only few genes with a therapeutic potential are mentioned within this studies (e.g. vascular endothelial growth factor (VEGF); the oncoprotein bcl-2). (Fussenegger et al., 1998; Hartenbach and Fussenegger, 2005; Kramer et al., 2003; Moser et al., 2000; Weber et al., 2005).

Concerning the expression of taste receptors there is one report on dicistronic expression of mouse taste receptors (mT2R8/5; mT1R3) each fused to green fluorescent protein and linked via an IRES element to red fluorescent protein. This approach was applied to trace and localize the expression pattern of taste receptors in neurons (Sugita and Shiba, 2005).

SUMMARY OF ADVANTAGEOUS EMBODIMENTS OF THE INVENTION

Therefore, the technical problem underlying the present invention was to provide a cell based screening system for modulators of GPCRs, i.e. establishing a method which makes it possible to successfully identify important modulators of some selected GPCRs, preferably T1R-type taste GPCRs. It was a further problem underlying the present invention to provide means and methods for the isolation of identified modulators without undue burden.

The solution to the above mentioned technical problems is achieved by providing the embodiments characterized in the claims.

Therefore, specially preferred embodiments of the present invention are means and methods for the expression of heterodimeric T1R-type taste GPCRs, wherein the expression of these heterodimeric T1R-type taste GPCRs is effected by modulating the GPCR coding sequences as well as their expression in multicistronic operons.

DETAILED DESCRIPTION OF ADVANTAGEOUS EMBODIMENTS OF THE INVENTION

Figure 1:
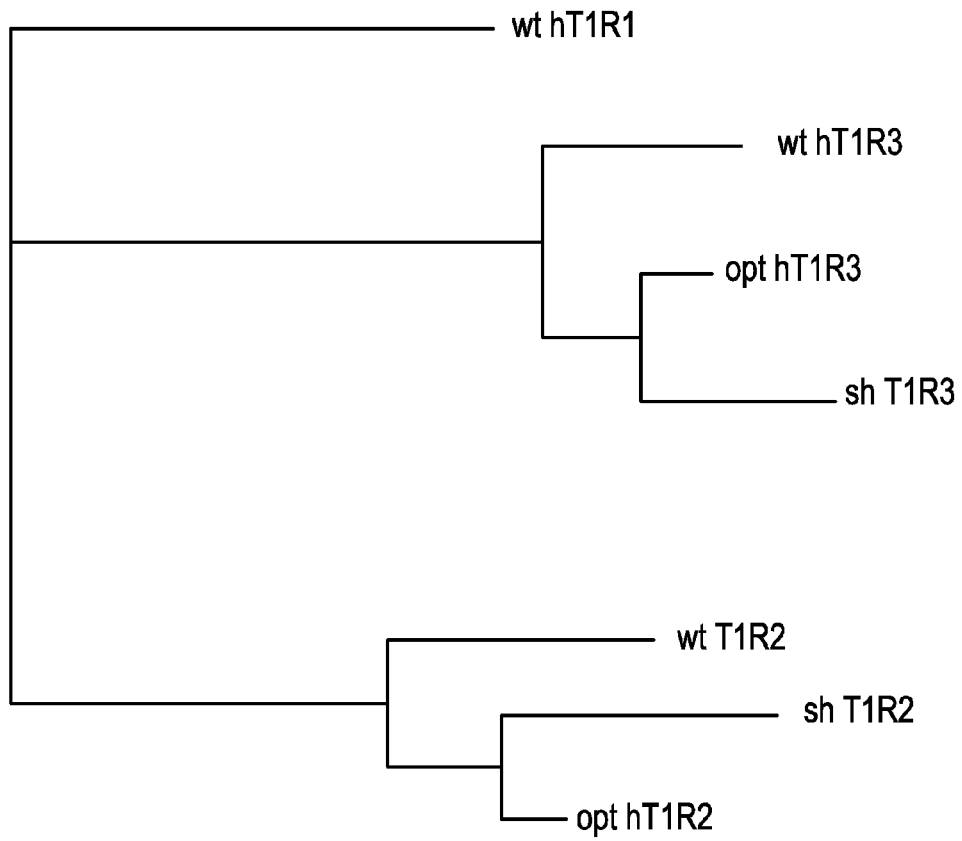
FIG. 1 depicts different GPCR nucleotide sequences of the T1R class, presented in an alignment analysis, with the underlying distance matrix shown below.

The above problem can surprisingly yet easily be solved by providing a method for the identification of modulators of GPCRs, comprising the steps of:
a. transforming eucaryotic host cells with genetic sequences coding for one or more than one GPCR(s),
b. cultivation of the transformed host cells under conditions sufficient to ensure the functional expression of said one or more GPCRs,
c. contacting the cultivated host cell expressing the one or more GPCRs in a functional manner with a potential modulator of the selected one or more GPCRs,
d. measuring a specific cellular response on exposure of the transformed host cell to the potential modulator, and
e. selecting an identificate, which induces a specific response.

Within the context of the present invention the term "modulator of GPCRs" is intended to mean a substance, which if applied in vivo, would (a) trigger an intracellular response by binding to the selected GPCR or (b) would inhibit such a response in the presence of a sweet compound. E.g. in the case of sweet receptors as the selected GPCR this modulator could be a substance which tastes sweet or which potentiates the sweetness of a sweet tasting compound without being sweet on its own or which inhibits the sweetness of sweet substances.

The term "conditions sufficient to ensure the functional expression" shall be understood as a summary of all conditions needed to ensure the functional expression of the GPCRs, rather than cell culture conditions. In a preferred embodiment of the present invention this term pertains to the vector used for transformation being a tricistronic vector. Further, this expression encompasses culturing cells which comprise a functional g-.protein. Under any circumstances, the functional expression of the GPCR(s) must be ensured.

The terms "functional expression" or "expressing in a functional manner" means within the context of the present invention that the selected receptor maintains its ability to interact specifically with the same substances the receptor would interact with in the in vivo situation.

By "selected cellular response" e.g. changes in intracellular calcium levels have to be understood, which can be measured easily e.g. by using dyes like Calcium 3, Fura-2, Fluo-4, Indo-1 or the calcium dependent reporter protein aequorin. Any cellular response related to the activity of the selected GPCRs is encompassed. Further examples of measuring the activity of GPCRs are (i) the activation of the second messenger cyclic adenosine monophosphate (cAMP) which can be quantified in GPCR dependent cell based assays with luminescent tags or with cAMP dependent reporter gene expression (e.g. Luciferase, SEAP or similar) or with the melanophore technology using frog skin cells; (ii) the measurement of β-arrestin binding to the targeted GPCR after ligand induced activation of the GPCR via bioluminescence resonance energy transfer (BRET) measurements or GFP-tagged β-arrestin movement imaging; (iii) measuring the agonist occupation of a GPCR and respectively the activation of the associated G-Protein, which can be quantified by using the radioactive, non-hydrolyzable analogue of GTP, [35S] GTPγS; (IV) the use of response element controlled reporter gene assays for the readout of GPCR activated interconnected pathways, including those involving MAP kinases, nonreceptor tyrosine kinases, receptor tyrosine kinases, phosphatidylinositol 3-kinases, and JNKs. (Eglen, 2005; Filmore, 2004; Milligan, 2003).

The term "identificate" is directed to a potential modulator after being identified as a true modulator of GPCR or the GPCR specific signaling cascade.

In a preferred embodiment the method is characterized in that the host cell is selected from the group consisting of: HEK293 (human embryo kidney), Hela (Human Negroid cervix epitheloid carcinoma), HT29 (Human Caucasian colon adenocarcinoma grade II), A431 (human squamous carcinoma), IMR 32 (human caucasian neuroblastoma), K562 (Human Caucasian chronic myelogenous leukaemia), U937 (Human Caucasian histiocytic lymphoma), MDA-MB-231 (Human Caucasian breast adenocarcinoma), SK-N-BE (2) (Human Caucasian neuroblastoma), SH-SY5Y (Human neuroblastoma), HL60 (human promyelocytic leukemia) or eukaryotic non-human cell lines like CHO-K1 (Hamster Chinese ovary), COS-7 (Monkey African green kidney, SV40 transformed), S49 (mouse lymphoma), Ltk (Mouse C34/an connective tissue), NG108-15 (Mouse neuroblastoma×Rat glioma hybrid), B50 (Rat nervous tissue neuronal, ECACC), C6 (Rat glial tumour), Jurkat (Human leukaemic T cell lymphoblast), BHK (Hamster Syrian kidney), Neuro-2a (Mouse Albino neuroblastoma), NIH/3T3 (mouse embryo fibroblast), preferably HEK293 (human embryo kidney), Hela (Human Negroid cervix epitheloid carcinoma), CHO-K1 (Hamster Chinese ovary) or Neuro-2a (Mouse Albino neuroblastoma).

It is essential that the host cell expresses a functional g-protein, preferably G-alpha15, either naturally or by means of genetic alteration of the host cell. Means for genetic alteration of eucaryotic cells are well known in the art, and need not to be discussed in depth here. The DNA-Sequences of G-proteins, e.g. G-alpha15 have already been described in the art.

A further preferred embodiment of the method of the present invention is characterized in that the one or more GPCR(s) is (are) selected from the group consisting of T1R or T2R taste receptors, preferably a T1R-type GPCR, especially T1R1, T1R2 and/or T1R3.

A further preferred embodiment of the method of the present invention is characterized in that two or more GPCRs are expressed in a heterologous co-expression of at least two different T1R-type GPCRs, preferably T1R1/T1R3, more preferably T1R2/T1R3.

A further preferred embodiment of the method of the present invention is characterized in that the transformation is accomplished with a multicistronic vector, preferably a tricistronic vector.

The vector of the present invention is an expression vector. By the term "expression vector" it is meant that the vector is used to transform a selected eucaryotic host cell, which, after transformation, expresses the gene or genes encoded by said vector. Expression vectors may be e.g. cloning vectors, binary vectors or integrating vector. Expression comprises transcription of the encoded nucleic acids into a functional (translatable) mRNA. Therefore, the respective control elements should be present, e.g. a sequence promoting transcription of the messenger (a promoter) and (optionally) a polyadenylation signal. Means for the expression of heterologous genes in eukaryotic cells are very well studied.

For the propagation of such vectors, usually prokaryotic cells such as $E.\ coli$ are used. Therefore, although the vectors of the present invention are designed to work as expression vectors in eukaryotic cells, they also carry elements for propagation in prokaryotic cells, e.g. an origin of replication (ori) and an antibiotics resistance gene, e.g. amp$^r$, kan$^r$ and similar. Means for the propagation of vectors in prokaryotes are well known in the art.

A list of possible eukaryotic expression vectors usable in the present invention, optionally usable for propagation in a prokaryotic host, and already commercially available comprises: pCR1000, pCDM8, pcDNA1, pcDNA1.1, pcDNA1/Amp, pcDNA1.1/Amp and pcDNA1/Neo, pcDNA3, pcDNA3.1, pcDNA3.2, pcDNA6.2, pDEST26, pDEST27, pCR3.1, pcDNA3.1 His, pDisplay (Invitrogen); pTriEx (pTriEx-2-Hygro) (Novagen); pSI, pCI (pCI-neo), pTargeT (Promega); pERV3, pFB-ERV, pCFB-EGSH, pDual, pCMV-Script (Stratagene); pNEBR (New England Biolabs), pEAK (Edge Biosystems).

A further preferred embodiment of the method of the present invention is characterized in that the multicistronic vector comprises a multicistronic expression unit comprising downstream from a promoter for the expression in an eucaryotic host and functionally linked thereto, the following cistrons:
 a. GPCR$_1$
 b. GPCR$_2$ and
 c. a selection marker,
wherein the promoter preferably is a strong promoter suitable for use in the selected host cell, more preferably being selected from the group consisting of cytomegalovirus promoter (P-CMV), human elongation factor 1 alpha promoter (P-E1α), human ubiquitin promoter (P-ubi), simian virus promoter (P-SV40), Rous sarcoma virus long terminal repeat promoter (P-RSV-LTR) and similar, wherein the GPCR$_1$ and the GPCR$_2$ are independently from another being selected from the group consisting of T1R or T2R taste receptors, preferably of the group of T1R receptors, more preferably a combination of T1R1-T1R3 or T1R2-T1R3, wherein the selection marker is being selected from the group consisting of hygromycin$^r$, zeocin$^r$, neomycin$^r$, blasticidin$^r$ or puromycin$^r$, and wherein both the GPCR1 and the GPCR2 as well as the selection marker are functionally connected by intervening IRES selected from the group consisting of IRES$_{EMCV}$, derived from encephalomyocarditis virus (synonym: CITE$_{EMCV}$); IRES$_{GTX}$, derived from the GTX homeodomain mRNA; IRES$_{Rbm3}$, derived from cold-inducible Rbm3; IRES$_{PV}$, derived of polioviral origin, IRES$_{RV}$, derived from rhinovirus, IRESFMDV, derived from food and mouth disease virus; IRE$_{HV}$, derived from hepatitis C virus, IRES$_{CSFV}$, derived from classic swine fever virus, IRES$_{BVDV}$, derived from bovine viral diarrhea virus; IRES$_{FMLV}$, derived from friend murine leukemia virus gag mRNA; IRES$_{MMLV}$, derived from moloney murine leukemia virus gag mRNA; IRES$_{HIV}$, derived from human immunodeficiency virus env mRNA; IRES$_{PSIV}$, derived from $Plautia\ stali$ intestine virus; IRES$_{RPV}$, derived from $Rhopalosiphum\ padi$ virus; IRES$_{KSH}$, derived from Karposi's sarcoma-associated herpesvirus, preferably the IRES$_{EMCV}$ being derived from encephalomyocarditis virus (synonym: CITE$_{EMCV}$) and wherein the multicistronic expression unit is terminated by a polyadenylation signal.

The term "functionally linked thereto" means within the context of the present invention that the components described are linked together to function in their intended manner.

A further preferred embodiment of the method of the present invention is characterized in that the multicistronic vector additionally comprises a genetic sequence coding for a g-protein or an equivalent thereof, preferably G-alpha 15 or an equivalent thereof, which is coded as an monocistronic unit consisting of a promoter, the gene of the selected g-protein and a polyadenylation site.

A further preferred embodiment of the method of the present invention is characterized in that the multicistronic vector additionally comprises a genetic sequence coding for a g-protein or an equivalent thereof, preferably G-alpha 15 or an equivalent thereof, which is coded as a fourth cistron in a quadrocistronic arrangement via an additional IRES element.

A further preferred embodiment of the method of the present invention is characterized in that the multicistronic vector additionally comprises a genetic sequence coding for a g-protein or an equivalent thereof, preferably G-alpha 15 or an equivalent thereof, the g-protein preferably being fused in-frame to above GPCR$_1$ and/or GPCR$_2$.

According to the present invention G proteins such as G-alpha15 or G-alpha16 or other promiscuous G proteins or G protein variants, or an endogenous G protein like gustducin, or another g-protein that when expressed in association with the multicistronically encoded GPCR(s) produces a functional read out may be used. In addition, G-beta and G-gamma proteins may also be used.

Subvariants of G-alpha 15 and/or G-alpha 16 with modified N-termini are also well known in the art, and can be used accordingly.

Essentially any chemical compound can be employed as a potential modulator or ligand in the assays according to the present invention. Compounds tested as G-protein coupled receptor modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluke Chemika-Biochemica Analytika (Buchs, Switzerland), for example. Also, compounds may be synthesized by methods known in the art.

So-called high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, Int. J. Pept. Prot. Res., 37:487-493; and Houghton et al., 1991, Nature, 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90:6909-6913), vinylogous polypeptides (Hagihara et al., 1992, J. Amer. Chem. Soc., 114:6568), non-peptidal peptidomimetics with glucose scaffolding (Hirschmann et al., 1992, J. Amer. Chem. Soc., 114:9217-9218), analogous organic synthesis of small compound libraries (Chen et al., 1994, J. Amer. Chem. Soc., 116:2661), oligocarbamates (Cho et al., 1993, Science, 261:1303), and/or peptidyl phosphonates (Campbell et al., 1994, J. Org. Chem., 59:658), nucleic acid libraries (see Ausubel, Berger and Sambrook, all supra), peptide nucleic acid libraries (U.S. Pat. No. 5,539,083), antibody libraries (e.g., Vaughn et al., 1996, Nature Biotechnology, 14(3):309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another aspect, the present invention encompasses screening and small molecule (e.g., drug) detection assays which involve the detection or identification of small molecules that can bind to a given protein, i.e., a taste receptor polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

Compounds which are identified according to the methods provided herein, and which modulate or regulate the biological activity or physiology of the T1R polypeptides according to the present invention are a preferred embodiment of this invention. It is contemplated that such modulatory compounds may be employed as outlined above.

Assays that may be utilized with one or more T1Rs according to the invention include by way of example assays that utilize a genetic selection for living cells; assays that utilize whole cells or membrane fragments or purified taste receptor proteins; assays that utilize second messengers such as cAMP and IP3, assays that detect the translocation of arrestin to the cell surface, assays that detect the loss of receptor expression on the cell surface (internalization) by tested ligands, direct ligand-binding assays, competitive-binding assays with inhibitors, assays using in vitro translated protein, assays that detect conformational changes upon the binding of a ligand (e.g., as evidenced by proteolysis, fluorescence, or NMR), behavioral assays that utilize transgenic non-human animals that express a taste GPCR or a combination thereof, such as flies, worms, or mice, assays that utilize cells infected with recombinant viruses that contain taste GPCR genes, preferably measuring the change of intracellular calcium levels relative to intracellular calcium levels without contacting the cell to the modulator.

A further preferred embodiment of the method of the present invention is characterized in that the change is an increase.

A further preferred embodiment of the method of the present invention is characterized in that the change is an increase relative to intracellular calcium levels when the cell is contacted by a modulator in the presence of a sweet compound thereby enhancing the calcium level above the level of the level generated by the sweet compound alone. In this case the modulator can either be sweet on its own or either be a tasteless compound without having an bioactive potential to activate T1Rs or combinations thereof on its own. The sweet compound preferably being selected from the group consisting of glucose, fructose, saccharose, acesulfam K, saccharin, cyclamat, aspartam, xylitol, stevioside, sucralose, thaumatin, monellin, brazzein, perillartine, glycyrrhizin, sucronic acid, P-4000, SC45647, NC174, neohesperidin and sweet tasting amino acids, more preferably selected from the group consisting of glucose, fructose, saccharose or xylitol.

A further preferred embodiment of the method of the present invention is characterized in that the change is a decrease relative to intracellular calcium levels when the cell is contacted by a sweet compound instead of the modulator, the sweet compound preferably being selected from the non-exclusive group consisting of glucose, fructose, saccharose, acesulfam K, saccharin, cyclamat, aspartam, xylitol, stevioside, sucralose, thaumatin, monellin, brazzein, perillartine, glycyrrhizin, sucronic acid, P-4000, SC45647, NC174, neohesperidin and sweet tasting amino acids.

A still further preferred embodiment of the present invention are multiparameter optimized nucleic acid molecules coding for a GPCR, preferably a T1R-type GPCR, more preferably a T1R1, T1R2 or T1R3 or a functionally equivalent receptor protein, and even more preferably coding for proteins consisting of the amino acids sequences according to SEQ ID NO: 1 and/or SEQ ID NO: 2 or, optionally, functionally equivalent proteins.

These nucleic acid molecules in a preferred embodiment have the sequence as depicted in SEQ ID NOs 3 and 4.

Nucleic acid molecules which are functionally equivalent to the molecules as depicted in SEQ ID NOs 3 and 4 are also encompassed by the present invention.

Within the context of the present invention, functionally equivalent proteins have the same or a very similar function in-vivo. Preferably, functionally equivalent proteins share at least 60%, more preferably at least 80%, especially at least 90%, advantageously at least 99% identity in their amino acid sequence.

A functionally equivalent nucleic acid codes for a functionally equivalent protein and it is optimized for expression in a eucaryotic cell. According to a multiparameter optimization the codon usage was adapted to the codon bias of *Homo sapiens* genes. In addition, regions of very high (>80%) or very low (<30%) GC content have been avoided where possible. During the optimization process following cis-acting sequence motifs were avoided:

a) internal TATA-boxes, chi-sites and ribosomal entry sites
b) AT-rich or GC-rich sequence stretches
c) ARE, INS, CRS sequence elements
d) repeat sequences and RNA secondary structures, as well as
e) (cryptic) splice donor and acceptor sites, branch points.

The optimization process, starting from the human wild type sequences (wt_hT1R) revealed several sequences; surprisingly the sequences which offered the best performance (sh_T1R) in generating functional stable cell lines on the basis of the multicistronic expression approach were not those with the theoretically optimal sequence (opt_hT1R) nor the wild type sequences. The differences of the here exemplified sequences are illustrated as a phylogenetic alignment (generated by the bioinformatic software clustal X) with an accompanying relational distance matrix in FIG. 1.

A very preferred embodiment of the present invention are multicistronic expression vectors comprising more than one cistron coding for a GPCR.

The said multicistronic expression vector preferably comprises downstream from a promoter for the expression in an eucaryotic host cell and functionally linked thereto, the following cistrons:

a. $GPCR_1$
b. $GPCR_2$ and a
c. selection marker, wherein the promoter preferably is a strong promoter, more preferably being selected from the group consisting of cytomegalovirus promoter (P-CMV), human elongation factor 1 alpha promoter (P-E1α), human ubiquitin promoter (P-ubi), simian virus promoter (P-SV40), Rous sarcoma virus long terminal repeat promoter (P-RSV-LTR) and similar wherein the $GPCR_1$ and the $GPCR_2$ are independently from another being selected from the group consisting of T1R or T2R taste receptors, preferably of the group of T1R receptors, more preferably a combination of T1R1-T1R3 or T1R2-T1R3, and wherein the selection marker is being selected from the group consisting of hygromycin$^r$, zeocin$^r$, neomycin$^r$, blasticidin$^r$ or puromycin$^r$, and wherein both the GPCR1 and the GPCR2 as well as the selection marker are functionally connected by intervening IRES selected from the group consisting of $IRES_{EMCV}$, derived from encephalomyocarditis virus (synonym: $CITE_{EMCV}$); $IRES_{GTX}$, derived from the GTX homeodomain mRNA; $IRES_{Rbm3}$, derived from cold-inducible Rbm3; $IRES_{PV}$, derived of polioviral origin, $IRES_{RV}$, derived from rhinovirus, IRESFMDV, derived from food and mouth disease virus; $IRE_{HV}$, derived from hepatitis C virus, $IRES_{CSFV}$, derived from classic swine fever virus, $IRES_{BVDV}$, derived from bovine viral diarrhea virus; $IRES_{FMLV}$, derived from friend murine leukemia virus gag mRNA; $IRES_{MMLV}$, derived from moloney murine leukemia virus gag mRNA; $IRES_{HIV}$, derived from human immunodeficiency virus env mRNA; $IRES_{PSIV}$, derived from *Plautia stali* intestine virus; $IRES_{RPV}$, derived from *Rhopalosiphum padi* virus; $IRES_{KSH}$, derived from Karposi's sarcoma-associated herpesvirus, preferably, the $IRES_{EMCV}$, derived from encephalomyocarditis virus (synonym: $CITE_{EMCV}$) and wherein the multicistronic expression unit is terminated by a polyadenylation signal.

Another preferred embodiment of the present invention is a multicistronic vector as defined above, the vector additionally comprising a cistron coding for a G-protein, preferably G-alpha 15, the g-protein preferably being located between the last GPCR and the selection marker and being functionally connected to both of them via an IRES element as defined supra.

A further preferred embodiment are cell lines transformed with the vectors of the present invention. Respective eukaryotic cell lines are amphibian, worm, insect or mammalian cells such as CHO, Hela, Hek-293 and the like, e.g., cultured cells, explants, and cells in vivo.

Preferably, the host cell is selected from the group consisting of: HEK293 (human embryo kidney), Hela (Human Negroid cervix epitheloid carcinoma), HT29 (Human Caucasian colon adenocarcinoma grade II), A431 (human squamous carcinoma), IMR 32 (human caucasian neuroblastoma), K562 (Human Caucasian chronic myelogenous leukaemia), U937 (Human Caucasian histiocytic lymphoma), MDA-MB-231 (Human Caucasian breast adenocarcinoma), SK-N-BE(2) (Human Caucasian neuroblastoma), SH-SY5Y (Human neuroblastoma), HL60 (human promyelocytic leukemia) or eukaryotic non-human cell lines like CHO-K1 (Hamster Chinese ovary), COS-7 (Monkey African green kidney, SV40 transformed), S49 (mouse lymphoma), Ltk (Mouse C34/An connective tissue), NG108-15 (Mouse neuroblastoma×Rat glioma hybrid), B50 (Rat nervous tissue neuronal, ECACC), C6 (Rat glial tumour), Jurkat (Human leukaemic T cell lymphoblast), BHK (Hamster Syrian kidney), Neuro-2a (Mouse Albino neuroblastoma), NIH/3T3 (mouse embryo fibroblast), preferably HEK293 (human embryo kidney), Hela (Human Negroid cervix epitheloid carcinoma), CHO-K1 (Hamster Chinese ovary) or Neuro-2a (Mouse Albino neuroblastoma).

Further, preferred embodiments of the present invention are the modulators of GPCRs identifiable by the methods of the present invention and further characterized by being selected from the group consisting of sugars, steroids, tannins and lignans, terpenes, quinons, macrocycles, heterocycles, N-heterocycles and O-heterocycles, aliphatics and polyketides, flavonoids, proteins, peptides and amino acids, alkaloids and arenes, as stated above.

The intense investigations of the present inventors that led to the establishment of the method of the present invention showed that the recombinant co-expression of said taste receptors as stable integrants of eukaryotic host cells is hampered by a common instability. Although the phenomenon is far away from being understood, it might be possible that the expression and specific signal transduction of these T1R-type receptors interferes in a negative fashion with the cell physiology of such stable host cells.

Within the context of the present invention, an instable integration is characterized by a rapid loss of functionality within the first 10 passages of a selected recombinant cell line clone. Within these first ten passages it becomes obvious that more and more cells of a selected recombinant clone loose their characteristic functional taste GPCR expression, indicated by passage dependent incremental decrease of sweetener induced calcium inductions (Fluo-4 measurements). By way of contrast, the stable integrants of the present invention are characterized in that they show a functional expression of said taste receptors at least over 50 passages, indicated by stable sweetener induced calcium inductions (Fluo-4 measurements) with a selected taste receptors expressing cell line clone.

As becomes clear from the present specification of the invention, the use and the hetero-oligomeric expression of the taste receptor combinations T1R1/T1R3 and more preferred T1R2/T1R3 to identify compounds as modulators of sweet taste in the field of tastants are especially preferred embodiments of the present invention.

Accordingly, this invention relates to recombinantly engineered T1R-type GPCRs having activity in cell based tastant assays, obtainable by (a) improving the coding sequence of the human sweet taste receptors (T1Rs) and/or (b) cloning them in a multicistronic expression unit for coordinated expression and simultaneous selection for the generation of stable eucaryotic cell systems; and/or (c) tagging one or both GPCRs in the hetero-dimeric expression complex with G-proteins or G-Protein chimeras to enable an improved fluorescence read out for the identification of GPCR modulators, preferably sweet taste modulating compounds.

The receptor sequences applied for the here presented invention are furthermore examplified in Example 1. By adding a prefix the optimized receptors have been termed shT1R2 and shT1R3. The respective amino acid sequences are depicted in SEQ ID NOs 1 and 2, the respective nucleic acid sequences in SEQ ID NOs 3 and 4.

A further means of the present invention to overcome the instability of co-expressed GPCRs, preferably taste receptors T1R2 and T1R3 in stable cell line development is the construction of multicistronic transcription units. The method for obtaining a multicistronic expression vector for the simultaneous expression of taste receptors and a selection marker of the invention is further examplified in Example 2. As stated above the development of T1R2/T1R3 expressing stable cell lines e.g. Hek293, CHO, Hela for their use in cell based assay systems is hampered by upcoming instabilities within the ongoing eucaryotic cell cultivation process and passaging numbers. For the generation of stable cell lines in the art most often expression vectors are used were the selection marker, conferring resistance to e.g. neomycin, hygromycin, zeocin, blasticidin or puromycin, is in fact coded on the same plasmid vector under the control of a independent promoter.

This situation can be avoided if the receptors and the selection marker are encoded in a multicistronic transcription unit.

However, so far multicistronic expression vectors have been described only for the use of inducible protein expression e.g. for gene therapy applications (Fussenegger et al., 1998; Moser et al., 2000).

For the present invention the two taste receptors shT1R2 and shT1R3 have been cloned in the first and second position of a tricistronic expression unit, whereas the deaminase gene conferring resistance to the selection marker blasticidin was cloned into the third position of the expression unit. The tricistronic unit is under the control of the strong human elongation factor 1 alpha promoter and the genes in the second and third position are preceded by an IRES element to facilitate their translation initiation in the resulting mRNA.

So far an eight kb multicistronic expression system for the stable functional expression of membrane located GPCRs has not been described. Usually these multicistronic systems—already in expressions of much smaller gene products like fluorescent proteins—are characterized by a non-stoichiometric and decreasing expression with increased distance from the promoter. Since the taste GPCRs significantly exceed the size of GFP or genes so far used in tri- or quadrocistronic expression systems; and the fact that the GPCRs have to be co-expressed to form a heterodimeric protein complex to function as sweetener responsive receptors it was an unforeseeable and surprising result of the intense investigations leading to the present invention that only the use of multicistronic vectors, i.e. tri- or tetracistronic vectors let to satisfying results in establishing the screening method of the present invention.

In a further embodiment, this invention relates to methods using the before mentioned multicistronic expression vector to create stable cell lines suited to express T1R polypeptides to construct a cell based screening tool for the search of novel compounds in the field of sweet taste modulators. Preferably, the cells comprise a functional G protein, e.g., G-alpha-15, G-alpha-16 or chimeric G protein like the ones with altered c-terminus previously identified:

a) substitution of the last five amino acids of G-alpha 15:
G-alpha__15 (EINLL), replaced with EYNLV (G-alpha q and G-alpha 11), EFNLV (G-alpha 14), QYELL (G-alpha s and G-alpha olf), DCGLF (G-alpha i1, G-alpha i2, G-alpha t1, G-alpha t2, and G-alpha gust), ECGLY (G-alpha i3), GCGLY (G-alpha o1 and G-alpha o2), YIGLC (G-alpha z), DIMLQ (G-alpha 12), QLMLQ (G-alpha 13) or G-alpha 16 replaced with ECGLY (G-alpha 16 i3)

b) substitution of the last 44 carboxy-terminal amino acids of G-alpha-16:
G-alpha 16gust44 (44 amino acids of the G-protein gustducin)
G-alpha 16z44 (44 amino acids of G-alpha-z);
G-alpha 16C44i2 (44 amino acids of the G-alpha-12);
G-alpha 16C44i3 (44 amino acids of the G-alpha-13);

or another G protein that is capable of coupling the chimeric receptor to an intracellular signaling pathway or to a signaling protein such as phospholipase C. (Li et al., 2002; Offermanns, 2003; Offermanns and Simon, 1995; Ueda et al., 2003). For this purpose HEK 293 cells comprising a functional G protein have been transfected with the vector pTrix-Eb_R2R3, cultured in the presence of blasticidine, and stable cell lines have been selected. As shown in Example 3 such cells have been found to exhibit responses to taste stimuli and in addition these cell lines have—compared to those derived with monocistronic T1R expression vectors—a pronounced stable expression of the T1R polypeptides. A stable cell line based on the expression vector pTrix-Eb_R2R3 (see example 3) shows calcium responses to several artificial sweeteners and a natural sweet protein. These responses can still be measured after more than 50 passages of the clone under selection with blasticidin and G418. Such results could not be achieved with monocistronic or bicistronic expressions. RT-PCR results of monocistronic clones revealed the loss of both receptors with the initial 5 to 10 passages under selection conditions. The stable cell line HEK_Ga15#17R2R3b #8 also shows dosis-dependent calcium responses for the above shown sweet tastants which correlated with physiological taste responses.

A further unexpected effect is that these multicistronic stable taste receptor expressing cell lines are well suited for natural compound screening using complex microbial extract preparations. For the isolation and preparation of such complex screening samples standard microbial methods can be applied which encompass the cultivation of microorganisms. Bioactive metabolites of interest from such cultivations may include intracellular molecules as well as those secreted into the cultivation media. Depending on the number of samples to be processed, a choice can generally be made from different options: (i) heating of the whole broth; (ii) filtration of broth supernatant through a high molecular weight exclusion filter with subsequent freeze-drying of the filtrate; (iii) extraction of either the whole broth (ultrasonication, french press, cell disruption bombs or similar devices) or the broth supernatant with organic solvents of varying polarity (e. g. chloroform, aceton, methanol or ethyl acetat) followed by evaporation of the extracts to dryness. (iv) Mixing the whole broth or the broth supernatant with resins (e.g. AMBERLITE®, XAD-2, XAD-4, XAD-9 or similar) with subsequent solid phase extraction with organic solvents (e.g. acetone, acetic acid, butanol, ethanol, ethyl acetate, methanol, polyglycols or similar) either fractionated by applying increasing solvent concentrations or as whole batch by applying the pure solvent without fractionation. Solid phase extracts can be used directly in suited assay systems or further evaporated to dryness and resolved under standardized conditions for subsequent testing, e.g. the activation of taste receptors in cell based assays. Activation of T1R receptors in such cells can be detected using any standard methods, such as by detecting changes in intracellular calcium by detecting Fluo-4 dependent fluorescence in the cell. Such an assay is the basis of the experimental findings presented in this application.

In a similar manner plant extracts well known to the skilled man may be used as well.

Figure 3:
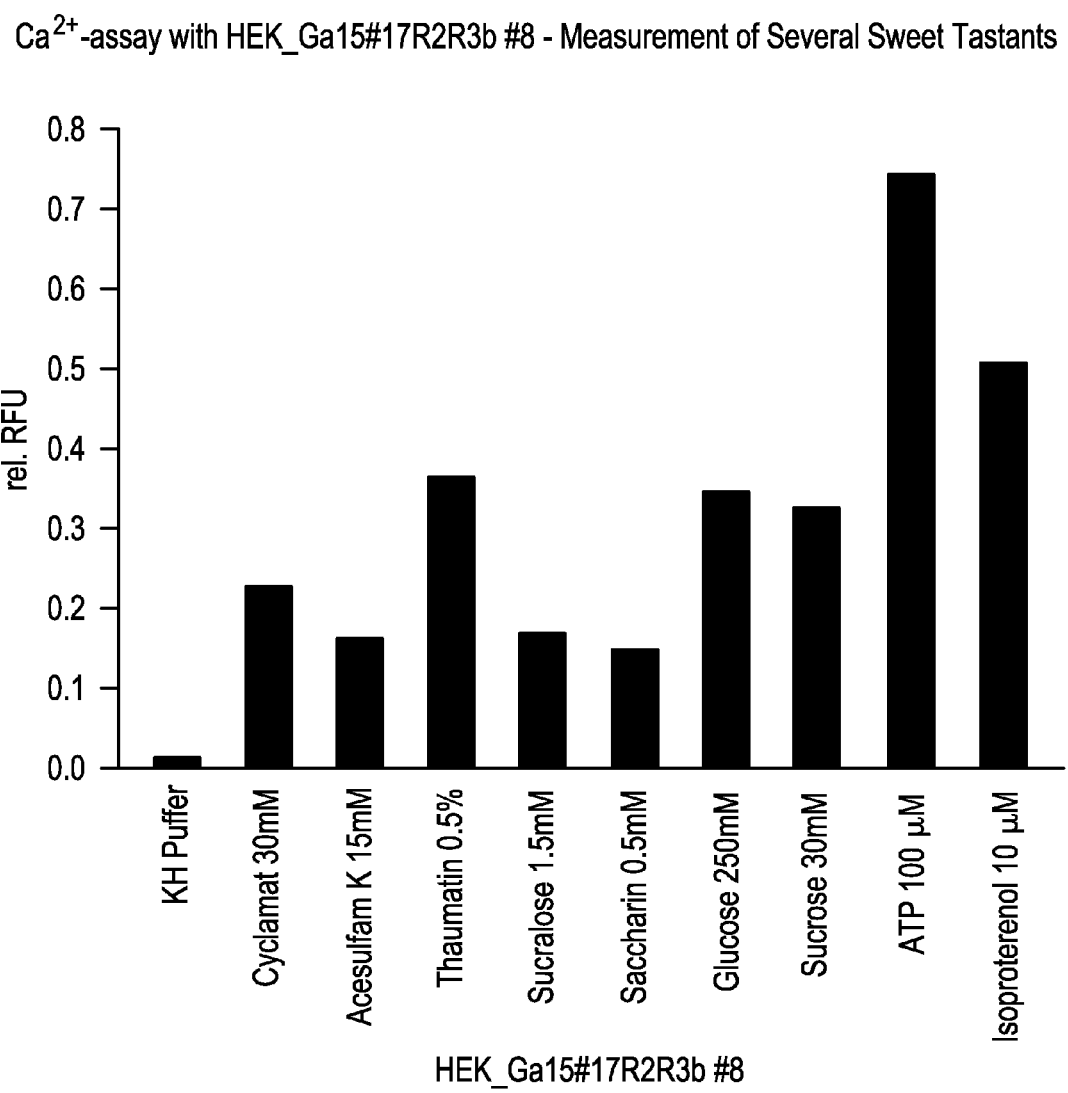
FIG. 3 depicts a $Ca^{z+}$-assay with HEK_Ga15#17R2R3b #8 measuring several sweet tastants.

In FIG. 3 the activity of a stable cell line derived with the multicistronic expression plasmid pTrix-Eb-R2R3 in a G-alpha 15 G-Protein background is depicted. The data of FIG. 3 document that these cell line amongst several other isolated cell lines, shows T1R2/T1R3 dependent activity in cell based assays towards several tastants like cyclamate, D-phenylalanine, saccharin, acesulfam K, aspartam and thaumatin.

In a further embodiment, this invention relates to the use of T1R-G-protein fusion genes for the development of T1R-dependent cell based assays. It has been shown that GPCRs can be fused in frame with different polypeptides without loosing their functional activity (Milligan et al., 2003). From the present data it cannot be foreseen that a fusion of a functional G-Protein to any GPCR leads to an improved activity compared to the wild type unfused situation. However it is scheduled to develop T1R2- and/or T1R3-fusion proteins in which the T1R-GPCR is fused to a functional G-Protein which is able to connect the T1R dependent signaling to the calcium inducing pathways used for T1R dependent activity measurement in cell based assays as exemplified in Example 3. Preferably, the T1R-fusion proteins comprise a functional G protein, e.g., Galpha-15 or chimeric G protein like the ones previously identified, or another G protein that is capable of coupling the chimeric receptor to an intracellular signaling pathway or to a signaling protein such as phospholipase C. (Offermanns, 2003; Offermanns and Simon, 1995; Ueda et al., 2003) For the development of such cell based assays the fusion proteins will be subcloned into the multicistronic expression vector backbone leading to expression vector of the type pTrix-Eb-R2Gq-R3 depicted in FIG. 4.

The figures show:

FIG. 1: Bioinformatic alignment with Clustal X software: Different GPCR nucleotide sequences of the T1R class are presented in an alignment analysis. Human wild type cDNA sequences are depicted as wt_hT1Rs; the theoretically most optimized cDNA sequences after multi parameter optimization are depicted as opt_hT1Rs; partly optimized cDNAs used for stable cell line development are termed sh_T1Rs. The nucleotide alignments are presented as phylogenetic trees in which wt_T1R1 was defined as the outgroup. The underlying distance matrix is shown below.

Figure 2:
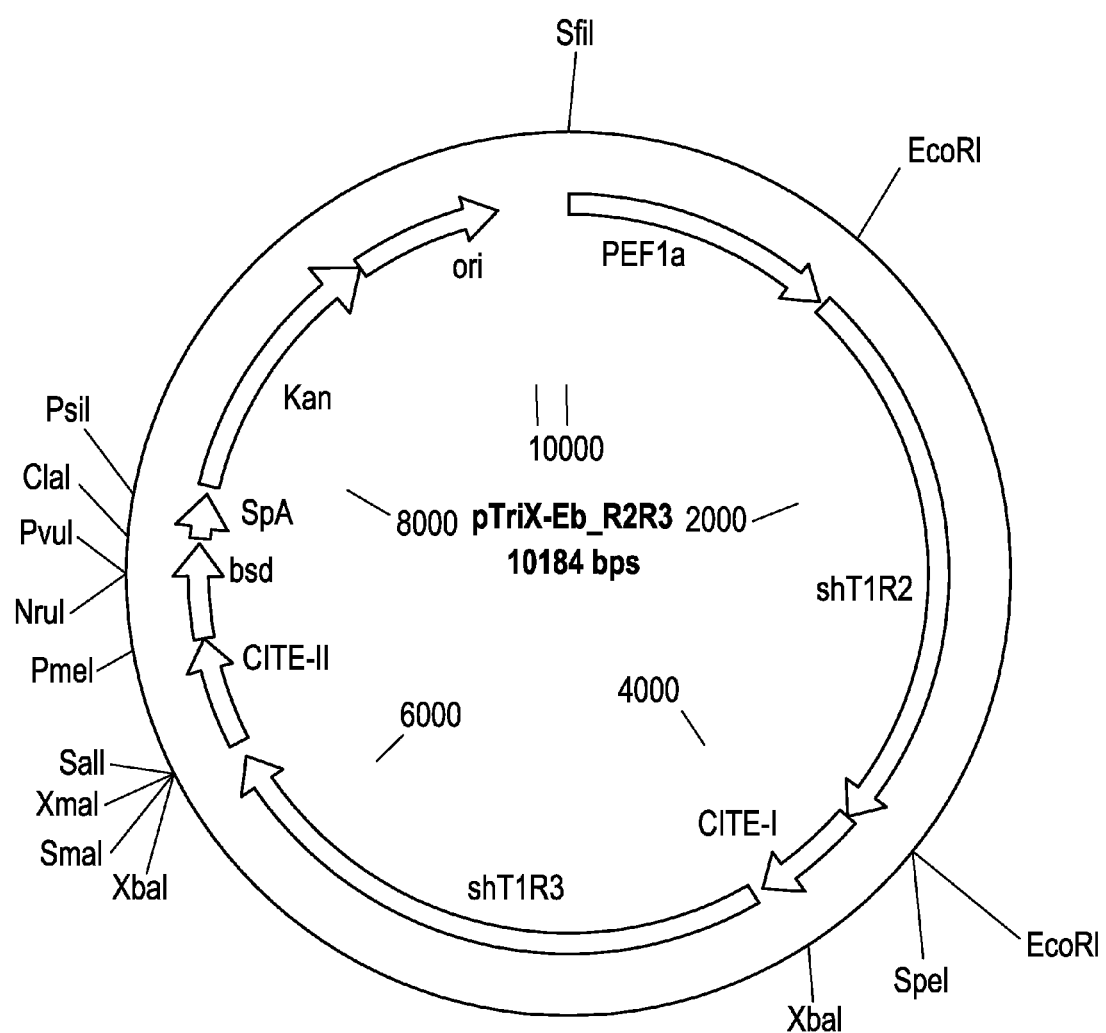
FIG. 2 depicts an exemplary multicistronic eukaryotic expression vector pTrix-Eb-R2R3.

FIG. 2: Multicistronic eucaryotic expression vector pTrix-Eb-R2R3: The expression of the taste receptor genes shT1R2, shT1R3 and blasticidin S deaminase (bsd) gene are under the control of the human elongation factor 1 alpha promoter (PEF1a). To confer multicistronic expression on the translational level two internal ribosomal entry sites (Cite I and Cite II) have been inserted. The multicistronic unit is terminated by a simian virus 40 polyadenylation site. The prokaryotic origin of replication (ori) and the kanamycin resistance gene serve for the propagation, amplification and selection of the plasmid vector in *E. coli*.

FIG. 3: The stable HEK_Ga15#17R2R3b #8 was selected with blasticidin and G418 after transfection of the stable HEK_Ga15#17 (G418) with pTriX_Eb_R2R3. This tricistronic expression was necessary for the selection and retrieval of stable clones. Clone #8 shows calcium responses to several artificial sweeteners and a natural sweet protein.

Figure 4:
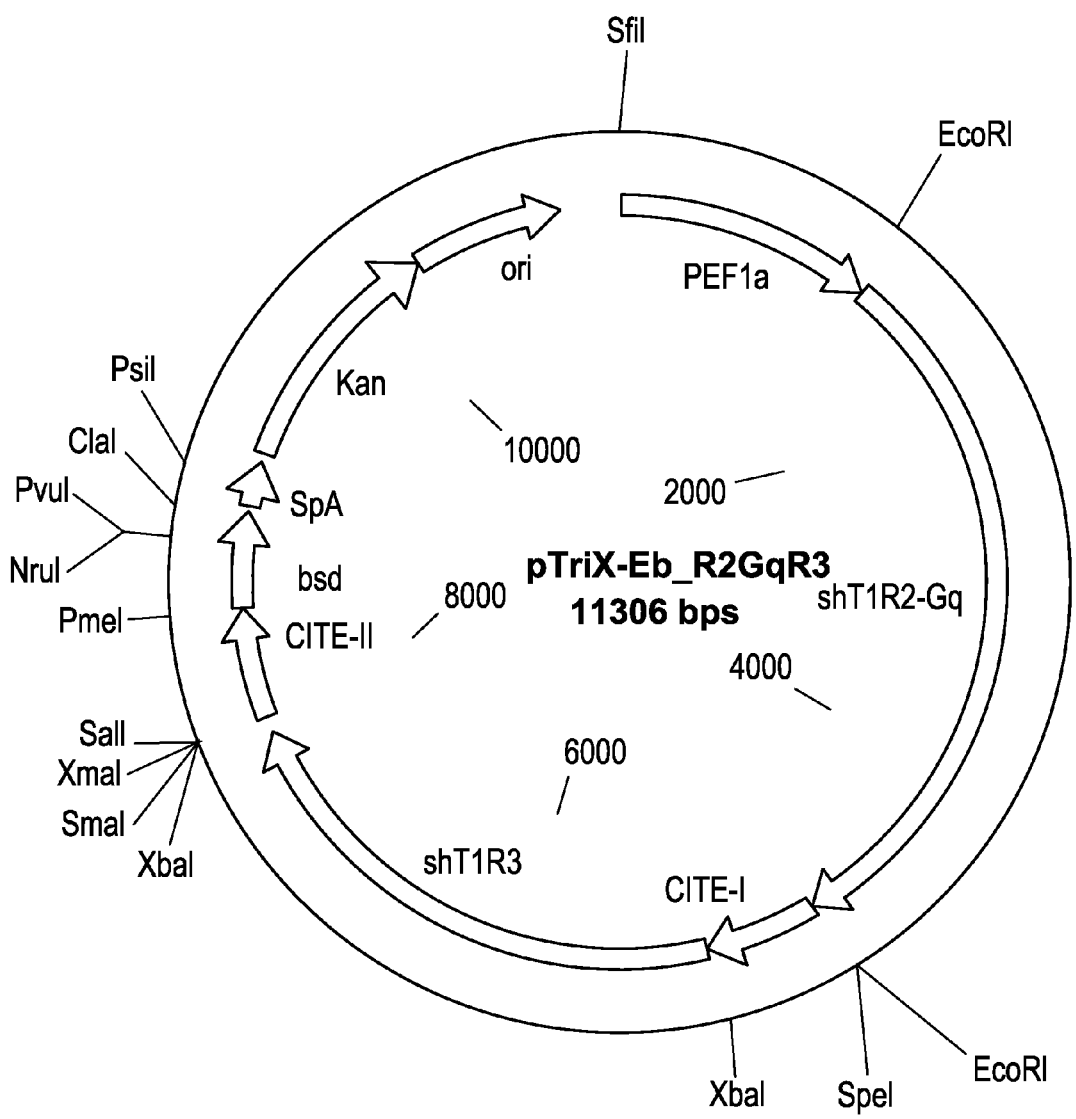
FIG. 4 depicts an alternative exemplary multicistronic eukaryotic expression vector p Trix-Eb-R2R3.

FIG. 4: Multicistronic eucaryotic expression vector pTrix-Eb-R2R3: The expression of the taste receptor genes shT1R2-Gq, shT1R3 and blasticidin S deaminase (bsd) gene are under the control of the human elongation factor 1 alpha promoter (PEF1a). To confer multicistronic expression on the translational level two internal ribosomal entry sites (Cite I and Cite II) have been inserted. The multicistronic unit is terminated by a simian virus 40 polyadenylation site. The prokaryotic origin of replication (ori) and the kanamycin resistance gene serve for the propagation, amplification and selection of the plasmid vector in E. coli.

Experimental Materials and Methods

Cell Culture

Transient transfection/selection of stable HEK293 cells—Transient and stable transfections can be performed with lipid complexes like calcium phosphate precipitation, Lipofectamine/PLUS reagent (Invitrogen), Lipofectamine 2000 (Invitrogen) or MIRUS TransIT293 (Mirus Bio Corporation) according to the manuals. Electroporation can also be a method of choice for stable transfection of eukaryotic cells.

The cells are seeded in 6-well plates at a density of 4×105 cells/well. HEK293 cells are transfected with linearised plasmids for stable expression of the genes of interest. After 24 hours, the selection with selecting reagents like zeocin, hygromycin, neomycin or blasticidin starts. About 50 µl to 300 µl trypsinized transfected cells from a 6-well are seeded in a 100 mm dish and the necessary antibiotic is added in an appropriate concentration. Cells are cultivated until clones are visible on the 100 mm cell culture plate. These clones are selected for further cultivation and calcium imaging. It takes about four to eight weeks to select cell clones which stably express the genes of interest.

Calcium Imaging

Fluo-4 AM assay with stable HEK293 cells—Stable cells are maintained in DMEM high-glucose medium (Invitrogen) supplemented with 10% fetal bovine serum (Biochrom) and 4 mM L-glutamine (Invitrogen). Cells for calcium imaging are maintained in DMEM low-glucose medium supplemented with 10% FBS and 1× Glutamax-1 (Invitrogen) for 48 hours before seeding. These stable cells are trypsinized after 48 hours (either with Trypsin-EDTA, Accutase or TrypLE) and seeded onto poly-D-lysine coated 96-well assay plates (Corning) at a density of 45,000 cells/well in DMEM low-glucose medium supplemented with 10% FBS and 1× Glutamax-1.

After 24 hours, the cells were loaded in 100 µl medium with additional 100 µl of 4 µM Fluo-4 (calcium sensing dye, 2 µM end concentration; Molecular Probes) in Krebs-HEPES (KH)-buffer for 1 hour. The loading reagent is then replaced by 80 µl KH-buffer per well. The Krebs-HEPES-buffer is a physiological saline solution including 1.2 mM CaCl2, 4.2 mM NaHCO3 and 10 mM HEPES.

The dye-loaded stable cells in plates were placed into a fluorescence microtiter plate reader to monitor fluorescence (excitation 488 nm, emission 520 nm) change after the addition of 20 µl KH-buffer supplemented with 5× tastants. For each trace, tastant was added 11.5 seconds after the start of the scan and mixed two times with the buffer, scanning continued for an additional 32 seconds, and data were collected every second.

Data analysis/Data recording—Calcium mobilization was quantified as the change of peak fluorescence (ΔF) over the baseline level (F). Data were expressed as the mean S.E. of the ΔF/F value of replicated independent samples. The analysis was done with the software of the microtiter plate reader.

EXAMPLES

The following examples are provided to illustrate preferred embodiments and are intended to be illustrative and not limitative of the scope of the invention. In the DNA sequences presented herein, the one letter codes N or n refers to any of the of the four common nucleotide bases, A, T, C, or G. In the protein sequences presented herein, the one-letter code X or Xaa refers to any of the twenty common amino acid residues.

Example 1

Synthesis and Design of Synthetic Intronless hT1R2 and hT1R3 cDNAs

The nucleotide sequence of the human receptors hT1R2 and hT1R3 are based on their wild type coding DNAs and have been optimized according to a multiparameter analysis considering optimal codon usage, putative cryptic splice sites, putative repeated sequences as well as AT-rich or GC-rich sequence stretches. Gene optimization often has favorable effects on enhanced mRNA stability, translational efficiency and reduced RNA secondary structure to prevent transcriptional pausing or premature termination of transcriptional elongation.

Up to now the binding sites for only a few ligands of the sweet taste heterodimeric receptor T1R2/T1R3 are known. Hence, the encoded wild-type amino acid sequences of the receptors were left unchanged in this multiparameter optimization, to retain the receptors binding qualities.

Synthesis and construction of the receptor cDNAs was done via the assembly of synthetic oligonucleotides and subsequent cloning into a standard pUC-18 plasmid vector for further amplification. Alternatively, these nucleic acids can be cloned in vitro by well-known cloning techniques, (Ausubel et al., 1998; Pachuk et al., 2000; Sambrook et al., 1989; Stemmer et al., 1995). Double-stranded DNA fragments may then be obtained either by synthesizing the complementary strand and annealing the strands together under appropriate conditions, or by adding the complementary strand using DNA polymerase with an appropriate primer sequence.

Due to the synthetic generation of the cDNAs the receptors of the present invention have been described with the prefix "s" and termed shT1R2 and shT1R3. The nucleic acid and amino acid sequences for the above mentioned T1R cloned sequences as well as other full-length and partial T1R sequences are set forth in the sequence protocoll:

Example 2

Multicistronic Vectors for the Expression of Taste Receptors

For the construction of a multicistronic expression unit the taste receptor sequences displayed in Example 1 have been used. As shown in FIG. 2 the tricistronic expression unit is under the control of the human elongation factor 1 alpha promoter. Using standard cloning techniques the cDNA for the receptors shT1R2 and shT1R3 and the cDNA for the blasticidin S deaminase gene have been cloned. To enable the translation initiation of each gene of this tricistronic unit two EMC-virus derived internal ribosomal entry sites (IRES—also termed Cap-independent translation enhancer (CITE)) have been inserted. (Jackson et al., 1990; Jang et al., 1988) The tricistronic expression unit is terminated by a simian virus 40 polyadenylation signal sequence. This composition permits the simultaneous expression of all three genes under the control of only one promoter. In contrast to monocistronic transcription units, which integrate independently from each other into different chromosomal locations during the process of stable cell line development, the tricistronic transcription unit integrates all containing genes in one and the same chromosomal locus. Due to the alignment of the genes, the blasticidin S deaminase gene is only transcribed in case a full length transcription takes place. Moreover the polarity of multicistronic transcription units (Moser et al., 2000) leads probably to a balanced stoichiometry of the receptor genes and their expression rates in the range of 1:0.7 up to 1:1 for the first two positions whereas the blasticidin S deaminase gene compared to the receptor genes in the third position is expressed to a lesser extend. Assuming that for the functional heterodimeric receptor shT1R2/shT1R3 a 1:1 stoichiometry is needed the lesser polarity effects for the receptor genes promote the desired stoichiometry whereas the reduced expression of the deaminase promotes an integration locus with enhanced transcriptional activity.

Example 3

Detection of T1R2/T1R3 Dependent Activity

In wild type taste cells—e.g. in the human taste bud—signal transduction is presumably transduced by the G-proteins gustducin and/or by G-Proteins of the Galpha-i type. Encountering sweet ligands the heterodimeric taste receptor T1R2/T1R3 reacts with induction of second messenger molecules; either induction of the cAMP level in response to most sugars or induction of the calcium level in response to most artificial sweeteners. (Margolskee, 2002)

To analyze the function and activity of the heterodimeric T1R2/T1R3 taste receptor a calcium dependent cell based assay has been utilized. Briefly, synthetic T1R type taste receptors (as shown in Example 1) have been transfected with the plasmid vector pTrix-Eb-R2R3 (see Example 2) in a HEK293 cell line stably expressing the mouse G-alpha-15 G-protein. Selection of T1R2/T1R3 expressing cells has been performed by culturing the transfected cells in the presence of blasticidine.

For measurement of T1R2/T1R3 taste receptor dependent activity HEK293 cells stably expressing G-alpha-15, shT1R2 and shT1R3 were 4×104 seeded in 96-well plates and labeled with the calcium sensitive fluorescence dye Fluo4-AM (2 µM) in DMEM culture medium for one hour at 37° C. For the measurement in a fluorescence plate reader the medium was exchanged for KH-buffer and incubated for another 15 minutes at 37° C. Fluorescence measurement of the labeled cells was conducted in a Novostar fluorescence plate reader (BMG, Offenburg, Germany). Response to different tastants as depicted in FIG. 3 was recorded as Fluo4-AM fluorescence increase initiated through the T1R2/T1R3 dependent increase of the second messenger calcium. After obtaining calcium signals for each sample, calcium mobilization in response to tastants was quantified as the relative change (peak fluorescence F1–baseline fluorescence F0 level, denoted as dF) from its own baseline fluorescence level (denoted as F0). Though rel. RFU is dF/F0. Peak fluorescence intensity occurred about 20-30 sec after addition of tastants. The data shown were obtained from two independent experiments and done in triplicates.

REFERENCES

Ausubel, F. M., Brent, R., Kingston, R. E., Moore, D. D., Seidman, J. G., Smith, J. A., and Struhl, K. (1998). /Current protocols in molecular biolong. //V. B. Chanada, series ed. //New York: Wiley & Sons./

Bachmanov, A. A., Tordoff, M. G., and Beauchamp, G. K. (2001). Sweetener preference of C57BL/6ByJ and 129P3/J mice. /Chem Senses/ 26, 905-13.

Bai, M., Trivedi, S., and Brown, E. M. (1998). Dimerization of the extracellular calcium-sensing receptor (CaR) on the cell surface of CaR-transfected HEK293 cells. /J Biol Chem/ 273, 23605-10.

Bockaert, J., and Pin, J. P. (1999). Molecular tinkering of G protein-coupled receptors: an evolutionary success. /Embo J/ 18, 1723-9.

Buck, L., and Axel, R. (1991). A novel multigene family may encode odorant receptors: a molecular basis for odor recognition. /Cell/ 65, 175-87.

Eglen, R. (2005). An Overview of High Throughput Screening at G Protein Coupled Receptors. /Frontiers in Drug Design & Discovery/ 1, 97-111.

Filmore, D. (2004). It's a GPCR world. /Modern Drug Discovery/, 24-28.

Firestein, S. (2001). How the olfactory system makes sense of scents. /Nature/ 413, 211-8.

Fussenegger, M., Mazur, X., and Bailey, J. E. (1998). pTRIDENT, a novel vector family for tricistronic gene expression in mammalian cells. /Biotechnol Bioeng/ 57, 1-10.

Fux, C., Langer, D., Kelm, J. M., Weber, W., and Fussenegger, M. (2004). New-generation multicistronic expression platform: pTRIDENT vectors containing size-optimized IRES elements enable homing endonuclease-based cistron swapping into lentiviral expression vectors. /Biotechnol Bioeng/ 86, 174-87.

George, S. R., O'Dowd, B. F., and Lee, S. P. (2002). G-protein-coupled receptor oligomerization and its potential for drug discovery. /Nat Rev Drug Discov/ 1, 808-20.

Grenby, T. H. (1996): Advances in Sweeteners, $1^{st}$ edition, Blackie Academic & Professional, London.

Hartenbach, S., and Fussenegger, M. (2005). Autoregulated, bidirectional and multicistronic gas-inducible mammalian as well as lentiviral expression vectors. /J Biotechnol/.

Hellen, C. U., and Sarnow, P. (2001). Internal ribosome entry sites in eukaryotic mRNA molecules. /Genes Dev/ 15, 1593-612.

Hoon, M. A., Adler, E., Lindemeier, J., Battey, J. F., Ryba, N. J., and Zuker, C. S. (1999). Putative mammalian taste receptors: a class of taste-specific GPCRs with distinct topographic selectivity. /Cell/ 96, 541-51.

Hoon, M. A., and Ryba, N. J. (1997). Analysis and comparison of partial sequences of clones from a taste-bud-enriched cDNA library. /J Dent Res/ 76, 831-8.

Jackson, R. J., Howell, M. T., and Kaminski, A. (1990). The novel mechanism of initiation of picornavirus RNA translation. /Trends Biochem Sci/ 15, 477-83.

Jang, S. K., Krausslich, H. G., Nicklin, M. J., Duke, G. M., Palmenberg, A. C., and Wimmer, E. (1988). A segment of the 5' nontranslated region of encephalomyocarditis virus RNA directs internal entry of ribosomes during in vitro translation. /J Virol/ 62, 2636-43.

Kaupmann, K., Malitschek, B., Schuler, V., Heid, J., Froestl, W., Beck, P., Mosbacher, J., Bischoff, S., Kulik, A., Shigemoto, R., Karschin, A., and Bettler, B. (1998). GABA(B)-receptor subtypes assemble into functional heteromeric complexes. /Nature/ 396, 683-7.

Kinnamon, S. C., and Cummings, T. A. (1992). Chemosensory transduction mechanisms in taste. /Annu Rev Physiol/ 54, 715-31.

Kinnamon, S. C., and Margolskee, R. F. (1996). Mechanisms of taste transduction. /Curr Opin Neurobiol/ 6, 506-13.

Kitagawa, M., Kusakabe, Y., Miura, H., Ninomiya, Y., and Hino, A. (2001). Molecular genetic identification of a candidate receptor gene for sweet taste. /Biochem Biophys Res Commun/ 283, 236-42.

Kramer, B. P., Weber, W., and Fussenegger, M. (2003). Artificial regulatory networks and cascades for discrete multilevel transgene control in mammalian cells. /Biotechnol Bioeng/ 83, 810-20.

Kunishima, N., Shimada, Y., Tsuji, Y., Sato, T., Yamamoto, M., Kumasaka, T., Nakanishi, S., Jingami, H., and Morikawa, K. (2000). Structural basis of glutamate recognition by a dimeric metabotropic glutamate receptor. /Nature/ 407, 971-7.

Leatherhead Food R A (2000). Ingredients Handbook Sweeteners, 2$^{nd}$ edition, Leatherhead Publishing, Leatherhead, Surrey.

Li, X., Inoue, M., Reed, D. R., Huque, T., Puchalski, R. B., Tordoff, M. G., Ninomiya, Y., Beauchamp, G. K., and Bachmanov, A. A. (2001). High-resolution genetic mapping of the saccharin preference locus (Sac) and the putative sweet taste receptor (T1R1) gene (Gpr70) to mouse distal Chromosome 4. /Mamm Genome/ 12, 13-6.

Li, X., Staszewski, L., Xu, H., Durick, K., Zoller, M., and Adler, E. (2002). Human receptors for sweet and umami taste. /Proc Natl Acad Sci USA/ 99, 4692-6.

Lindemann, B. (1996a). Chemoreception: tasting the sweet and the bitter. /Curr Biol/ 6, 1234-7.

Lindemann, B. (1996b). Taste reception. /Physiol Rev/ 76, 718-66.

Lindemann, B. (2001). Receptors and transduction in taste. /Nature/ 413, 219-25.

Lush, I. E. (1989). The genetics of tasting in mice. VI. Saccharin, acesulfame, dulcin and sucrose. /Genet Res/ 53, 95-9.

Lush, I. E., Hornigold, N., King, P., and Stoye, J. P. (1995). The genetics of tasting in mice. VII. Glycine revisited, and the chromosomal location of Sac and Soa. /Genet Res/ 66, 167-74.

Maeda, T., Imanishi, Y., and Palczewski, K. (2003). Rhodopsin phosphorylation: 30 years later. /Prog Retin Eye Res/ 22, 417-34.

Margolskee, R. F. (2002). Molecular mechanisms of bitter and sweet taste transduction. /J Biol Chem/ 277, 1-4.

Max, M., Shanker, Y. G., Huang, L., Rong, M., Liu, Z., Campagne, F., Weinstein, H., Damak, S., and Margolskee, R. F. (2001). Tas1r3, encoding a new candidate taste receptor, is allelic to the sweet responsiveness locus Sac. /Nat Genet/ 28, 58-63.

McLaughlin, S. K., McKinnon, P. J., and Margolskee, R. F. (1992). Gustducin is a taste-cell-specific G protein closely related to the transducins. /Nature/ 357, 563-9.

Meyerhof, W., Behrens, M., Brockhoff, A., Bufe, B., and Kuhn, C. (2005). Human bitter taste perception. /Chem Senses/ 30 Suppl 1, i14-i15. Milligan, G. (2003). High-content assays for ligand regulation of G-protein-coupled receptors. /Drug Discov Today/ 8, 579-85.

Milligan, G., Ramsay, D., Pascal, G., and Carrillo, J. J. (2003). GPCR dimerisation. /Life Sci/ 74, 181-8.

Montmayeur, J. P., Liberles, S. D., Matsunami, H., and Buck, L. B. (2001). A candidate taste receptor gene near a sweet taste locus. /Nat Neurosci/ 4, 492-8.

Moser, S., Schlatter, S., Fux, C., Rimann, M., Bailey, J. E., and Fussenegger, M. (2000). An update of pTRIDENT multicistronic expression vectors: pTRIDENTs containing novel streptogramin-responsive promoters. /Biotechnol Prog/ 16, 724-35.

Nelson, G., Chandrashekar, J., Hoon, M. A., Feng, L., Zhao, G., Ryba, N. J., and Zuker, C. S. (2002). An amino-acid taste receptor. /Nature/ 416, 199-202.

Nelson, G., Hoon, M. A., Chandrashekar, J., Zhang, Y., Ryba, N. J., and Zuker, C. S. (2001). Mammalian sweet taste receptors. /Cell/ 106, 381-90.

O'Brien Nabors, L. (2001). Alternative Sweeteners, 3$^{rd}$ edition, Marcel Dekker, Inc., New York, Basel.

Offermanns, S. (2003). G-proteins as transducers in transmembrane signalling. /Prog Biophys Mol Biol/ 83, 101-30.

Offermanns, S., and Simon, M. I. (1995). G alpha 15 and G alpha 16 couple a wide variety of receptors to phospholipase C. /J Biol Chem/ 270, 15175-80.

Pachuk, C. J., Samuel, M., Zurawski, J. A., Snyder, L., Phillips, P., and Satishchandran, C. (2000). Chain reaction cloning: a one-step method for directional ligation of multiple DNA fragments. /Gene/ 243, 19-25.

Pierce, K. L., Premont, R. T., and Lefkowitz, R. J. (2002). Seven-transmembrane receptors. /Nat Rev Mol Cell Biol/ 3, 639-50.

Pin, J. P., Galvez, T., and Prezeau, L. (2003). Evolution, structure, and activation mechanism of family 3/C G-protein-coupled receptors. /Pharmacol Ther/ 98, 325-54.

Sainz, E., Korley, J. N., Battey, J. F., and Sullivan, S. L. (2001). Identification of a novel member of the T1R family of putative taste receptors. /J Neurochem/ 77, 896-903.

Salahpour, A., Angers, S., and Bouvier, M. (2000). Functional significance of oligomerization of G-protein-coupled receptors. /Trends Endocrinol Metab/ 11, 163-8.

Sambrook, J., Fritsch, E., and Maniatis, T. (1989). Molecular cloning. A Laboratory Manual. /In: second ed. //Cold Spring Harbor Laboratory Press. Cold Spring Harbor. N.Y./

Stemmer, W. P., Crameri, A., Ha, K. D., Brennan, T. M., and Heyneker, H. L. (1995). Single-step assembly of a gene and entire plasmid from large numbers of oligodeoxyribonucleotides. /Gene/ 164, 49-53.

Sugita, M., and Shiba, Y. (2005). Genetic tracing shows segregation of taste neuronal circuitries for bitter and sweet. /Science/ 309, 781-5.

Ueda, T., Ugawa, S., Yamamura, H., Imaizumi, Y., and Shimada, S. (2003). Functional interaction between T2R taste receptors and G-protein alpha subunits expressed in taste receptor cells. /J Neurosci/ 23, 7376-80.

Von Rymon Lipinski, G.-W., Schiweck, H. (1991). Handbuch Süßungsmittel—Eigenschaften und Anwendung, Behr's Verlag, Hamburg.

Weber, W., Malphettes, L., de Jesus, M., Schoenmakers, R., El-Baba, M. D., Spielmann, M., Keller, B., Weber, C. C., van de Wetering, P., Aubel, D., Wurm, F. M., and Fussenegger, M. (2005). Engineered *Streptomyces* quorum-sensing components enable inducible siRNA-mediated translation control in mammalian cells and adjustable transcription control in mice. /J Gene Med/ 7, 518-25.

White, J. H., Wise, A., Main, M. J., Green, A., Fraser, N. J., Disney, G. H., Barnes, A. A., Emson, P., Foord, S. M., and Marshall, F. H. (1998). Heterodimerization is required for the formation of a functional GABA(B) receptor. /Nature/ 396, 679-82.

Wong, G. T., Gannon, K. S., and Margolskee, R. F. (1996). Transduction of bitter and sweet taste by gustducin. /Nature/ 381, 796-800.

Zhao, F. L., Lu, S. G., and Herness, S. (2002). Dual actions of caffeine on voltage-dependent currents and intracellular calcium in taste receptor cells. /Am J Physiol Regul Integr Comp Physiol/ 283, R115-29.

That which is claimed:

1. A nucleic acid molecule coding for a G-protein coupled receptor (GPCR), wherein the nucleic acid molecule is SEQ ID NO: 4.

2. A multicistronic expression vector comprising more than two cistrons encoding a sweet taste T1R-type G-protein coupled receptor (GPCR), wherein the cistrons are connected via a cap independent translation enhancer (CITE) element and wherein one of the cistrons comprises the nucleic acid molecule of SEQ ID NO: 4.

3. An isolated cell line stably transfected with the expression vector of claim 2.

4. A monocistronic expression vector comprising a cistron that comprises the nucleic acid molecule of SEQ ID NO: 4.

5. An isolated cell line stably transfected with the expression vector of claim 4.

* * * * *

UNITED STATES PATENT AND TRADEMARK OFFICE
CERTIFICATE OF CORRECTION

| | |
|---|---|
| PATENT NO. | : 8,067,236 B2 |
| APPLICATION NO. | : 12/616361 |
| DATED | : November 29, 2011 |
| INVENTOR(S) | : Krohn et al. |

Page 1 of 1

It is certified that error appears in the above-identified patent and that said Letters Patent is hereby corrected as shown below:

In the Claims

Column 35, Claim 2, Lines 52-53, replace "comprising more than two" with --comprising two--.

Signed and Sealed this
Twenty-ninth Day of October, 2013

Teresa Stanek Rea
*Deputy Director of the United States Patent and Trademark Office*